(12) United States Patent
Wu et al.

(10) Patent No.: US 6,458,744 B2
(45) Date of Patent: Oct. 1, 2002

(54) PESTICIDAL COMPOUNDS AND COMPOSITIONS

(75) Inventors: Tai-Teh Wu, Chapel Hill; Andrew William Scribner, Durham, both of NC (US)

(73) Assignee: Aventis CropScience S. A., Lyons (FR)

( * ) Notice: Subject to any disclaimer, the term of this patent is extended or adjusted under 35 U.S.C. 154(b) by 0 days.

(21) Appl. No.: 09/796,651

(22) Filed: Mar. 2, 2001

Related U.S. Application Data

(60) Provisional application No. 60/186,313, filed on Mar. 2, 2000.

(51) Int. Cl.$^7$ .............. C07D 401/06; A01N 43/40
(52) U.S. Cl. .............. 504/105; 514/341; 514/406; 546/275.4; 548/364.1; 504/106
(58) Field of Search .............. 546/275.4; 548/375.1, 548/364.1; 514/341, 406; 504/105, 106

(56) References Cited

U.S. PATENT DOCUMENTS 5,580,843    12/1996    Stetter et al.

FOREIGN PATENT DOCUMENTS

| EP | 0352944 A1 | 1/1990 |
| EP | 0511845 A1 | 11/1992 |
| EP | 0234119 B1 | 8/1994 |
| EP | 0659745 A | 6/1995 |
| EP | 0295117 B1 | 4/2000 |
| JP | 11171702 | * 4/1996 |
| JP | 08311036 | * 11/1996 |

* cited by examiner

*Primary Examiner*—Joseph K. McKane
*Assistant Examiner*—Kamal Saeed
(74) *Attorney, Agent, or Firm*—Burns, Doane, Swecker & Mathis, L.L.P.

(57) ABSTRACT

The invention relates to 4-thiomethylpyrazole compounds of formula (I):

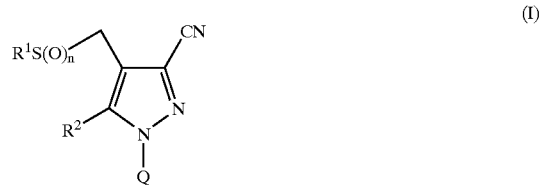

wherein $R^1$, $R^2$, Q and n are as defined in the description, and to their use as pesticides.

78 Claims, No Drawings

PESTICIDAL COMPOUNDS AND COMPOSITIONS

CROSS-REFERENCE TO RELATED APPLICATION

This application claims benefit of United States Provisional Patent Application No. 60/186,313, filed Mar. 2, 2000, incorporated by reference herein in its entirety and relied upon.

BACKGROUND OF THE INVENTION

1. FIELD OF THE INVENTION

The invention relates to new 4-thiomethylpyrazole compounds, related compounds, compositions containing them, processes for their preparation, and their use for the control of arthropod pests (especially insects) and nematodes.

2. DESCRIPTION OF THE RELATED ART

Pesticidal N-arylpyrazoles are described in the art, for example, in EP 0234119, EP 0511845, EP 0352944 and EP 0295117.

SUMMARY OF THE INVENTION

The present invention provides a compound of formula (I):

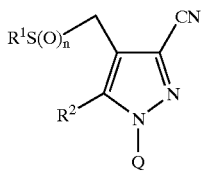

(I)

wherein:
Q is a group (A1) or (A2):

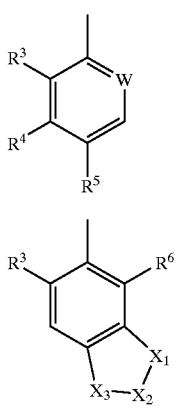

(A1)

(A2)

W is N or $CR^6$;
—$X_1$—$X_2$—$X_3$— is —$CF_2CF_2O$—, —$CF_2OCF_2$— or —$OCF_2O$—;
$R^1$ is alkyl, haloalkyl, alkenyl, haloalkenyl, alkynyl, haloalkynyl, cycloalkyl, cycloalkylalkyl or —$(CH_2)_mR^7$; or is naphthyl optionally substituted by alkyl, haloalkyl, halogen, $NO_2$, alkoxy, haloalkoxy or $R^8S(O)_p$;
$R^2$ is hydrogen, halogen or optionally substituted amino;

$R^3$ and $R^6$ are each independently hydrogen or halogen;
$R^4$ is hydrogen or haloalkyl;
$R^5$ is hydrogen, halogen, haloalkyl, haloalkoxy, —$S(O)_pCF_3$ or $SF_5$;
$R^7$ is phenyl or a five to seven membered heteroaromatic ring having from one to four heteroatoms which are the same or different selected from nitrogen, oxygen and sulfur, which ring is optionally substituted by $R^9$;
$R^8$ is alkyl or haloalkyl;
$R^9$ is alkyl, haloalkyl, halogen, CN, $NO_2$, $R^{10}O$, $R^8S(O)_p$, $C(O)R^8$, $C(O)OR^{10}$ or $NR^{10}R^{11}$; or when $R^7$ is phenyl two adjacent $R^9$ groups together form a —$CF_2OCF_2$— or —$OCF_2O$— group;
$R^{10}$ and $R^{11}$ are each independently hydrogen, alkyl or haloalkyl; and
m, n and p each independently have the value zero, one or two;
or an agriculturally acceptable salt thereof.

The compounds of formula (I) and the agriculturally acceptable salts thereof as defined above possess valuable pesticidal properties. The compounds of the invention show improved pesticidal activity in comparison with known compounds.

The invention also encompasses any stereoisomer, enantiomer or geometric isomer, or mixture thereof, of the compounds of formula (I).

By the term "agriculturally acceptable salts" is meant salts the cations or anions of which are known and accepted in the art for the formation of salts for agricultural or horticultural use. Suitable salts with bases include alkali metal (e.g. sodium and potassium), alkaline earth metals (e.g. calcium and magnesium), ammonium and amine (e.g. diethanolamine, triethanolamine, octylamine, morpholine and dioctylmethylamine) salts. Suitable acid addition salts, e.g. formed by compounds of formula (I) containing an amino group, include salts with inorganic acids, for example hydrochlorides, sulfates, phosphates and nitrates and salts with organic acids for example acetic acid.

DETAILED DESCRIPTION OF THE INVENTION

Unless otherwise specified, alkyl, acyl and alkoxy groups (or portions thereof) are straight- or branched- chain and have from one to ten (preferably one to six) carbon atoms.

Cycloalkyl groups have from three to six carbon atoms in the ring and are optionally substituted by alkyl or halogen.

Alkenyl and alkynyl groups or portions thereof are straight- or branched-chain and have from two to eight (preferably two to four) carbon atoms.

The term "halo" before the name of a radical means that this radical is partially or completely halogenated, that is to say, substituted by F, Cl, Br, or I, in any combination, preferably by F or Cl. The term "halogen" means F, Cl, Br or I.

A preferred embodiment of the invention comprises a compound of formula (I) wherein Q, $R^1$ and n are as defined above and $R^2$ is —$NR^{12}R^{13}$ or —$N$=$C(R^{10})(R^{14})$, wherein:
$R^{12}$ and $R^{13}$ are independently selected from hydrogen, alkyl, haloalkyl, alkenyl, haloalkenyl, alkynyl, haloalkynyl, —$C(O)R^{15}$ and $C(O)OR^{15}$; or $R^{12}$ and $R^{13}$ are joined together to form a divalent radical having 4 to 6 atoms in the chain, this divalent radical being alkylene, alkyleneoxyalkylene or alkyleneaminoalkylene (preferably forming a morpholine, pyrrolidine, piperidine or piperazine ring);

$R^{14}$ is alkoxy or haloalkoxy; or is phenyl optionally substituted by alkyl, haloalkyl, hydroxy, halogen, alkoxy, —S(O)$_p$R$^8$ or CN;

$R^{15}$ is alkenyl, haloalkenyl, alkynyl or haloalkynyl; or is alkyl optionally substituted by halogen, alkoxy, C(O)R$^8$, C(O)OR$^{10}$, CN, —S(O)$_p$R$^8$, or CONR$^{10}$R$^{11}$.

Preferred compounds of formula (I) are those in which $R^1$ is alkyl, haloalkyl, cycloalkyl or naphthyl; or phenyl optionally substituted by halogen, alkyl, haloalkyl, alkoxy, haloalkoxy or NO$_2$; or pyridyl optionally substituted by halogen or haloalkyl; or —CH$_2$R$^7$ wherein R$^7$ is phenyl optionally substituted by halogen, alkyl or alkoxy; or —CH$_2$CH$_2$R$^7$ wherein R$^7$ is phenyl.

Preferred compounds of formula (I) are those in which Q is a group (A1) wherein:
W is N or CR$^6$; R$^3$ and R$^6$ are each independently hydrogen or halogen; R$^4$ is hydrogen; and R$^5$ is halogen, CF$_3$, OCF$_3$ or SF$_5$; or wherein:
W is N or CR$^6$; R$^3$ and R$^6$ are each independently hydrogen or halogen; R$^4$ is CF$_3$; and R$^5$ is hydrogen.

More preferred compounds of formula (I) are those in which Q is a group (A1) wherein:
W is CR$^6$; R$^3$ is hydrogen or halogen; R$^6$ is halogen; R$^4$ is hydrogen; and R$^5$ is halogen, CF$_3$ or OCF$_3$; or wherein:
W is CR$^6$; R$^3$ is hydrogen; R$^6$ is halogen; R$^4$ is CF$_3$; and R$^5$ is hydrogen.

Preferred compounds of formula (I) are those in which $R^2$ is —NR$^{12}$R$^{13}$ or —N=C(R$^{10}$)(R$^{14}$).

More preferred compounds are those in which $R^2$ is —NR$^{12}$R$^{13}$ or —N=C(R$^{10}$)(R$^{14}$), wherein R$^{12}$ is hydrogen, alkyl or —C(O)R$^{15}$; R$^{13}$ is hydrogen or alkyl; R$^{10}$ is hydrogen; R$^{14}$ is alkoxy; and R$^{15}$ is alkyl.

Yet more preferred compounds are those in which $R^2$ is —NHR$^{13}$ or —N=CH(R$^{14}$); wherein R$^{13}$ is hydrogen or alkyl; and R$^{14}$ is alkoxy.

Compounds in which R$^2$ is amino are most preferred.

Compounds in which n is 1 or 2 are also preferred.

A preferred class of compounds of formula (I) are those in which:
$R^1$ is alkyl, haloalkyl, cycloalkyl or naphthyl; or phenyl optionally substituted by halogen, alkyl, haloalkyl, alkoxy, haloalkoxy or NO$_2$; or pyridyl optionally substituted by halogen or haloalkyl; or —CH$_2$R$^7$ wherein R$^7$ is phenyl optionally substituted by halogen, alkyl or alkoxy; or —CH$_2$CH$_2$R$^7$ wherein R$^7$ is phenyl;
Q is a group (A1) wherein:
W is N or CR$^6$; R$^3$ and R$^6$ are each independently hydrogen or halogen; R$^4$ is hydrogen; and R$^5$ is halogen, CF$_3$, OCF$_3$ or SF$_5$; or wherein:
W is N or CR$^6$; R$^3$ and R$^6$ are each independently hydrogen or halogen; R$^4$ is CF$_3$; and R$^5$ is hydrogen; and
$R^2$ is —NR$^{12}$R$^{13}$ or —N=C(R$^{10}$)(R$^{14}$); wherein R$^{12}$ is hydrogen, alkyl or —C(O)R$^{15}$; R$^{13}$ is hydrogen or alkyl; R$^{10}$ is hydrogen; R$^{14}$ is alkoxy; and R$^{15}$ is alkyl.

A further preferred class of compounds of formula (I) are those in which:
$R^1$ is alkyl, haloalkyl, cycloalkyl or naphthyl; or phenyl optionally substituted by halogen, alkyl, haloalkyl, alkoxy, haloalkoxy or NO$_2$; or pyridyl optionally substituted by halogen or haloalkyl; or —CH$_2$R$^7$ wherein R$^7$ is phenyl optionally substituted by halogen, alkyl or alkoxy; or —CH$_2$CH$_2$R$^7$ wherein R$^7$ is phenyl;

Q is a group (A1) wherein:
W is N or CR$^6$; R$^3$ and R$^6$ are each independently hydrogen or halogen; R$^4$ is hydrogen; and R$^5$ is halogen, CF$_3$, OCF$_3$ or SF$_5$; or wherein:
W is N or CR$^6$; R$^3$ and R$^6$ are each independently hydrogen or halogen; R$^4$ is CF$_3$; and R$^5$ is hydrogen;
$R^2$ is —NR$^{12}$R$^{13}$ or —N=C(R$^{10}$)(R$^{14}$); wherein R$^{12}$ is hydrogen, alkyl or —C(O)R$^{15}$; R$^{13}$ is hydrogen or alkyl; R$^{10}$ is hydrogen; R$^{14}$ is alkoxy; and R$^{15}$ is alkyl; and
n is 1 or 2.

A further preferred class of compounds of formula (I) are those in which:
$R^1$ is alkyl, haloalkyl, cycloalkyl or naphthyl; or phenyl optionally substituted by halogen, alkyl, haloalkyl, alkoxy, haloalkoxy or NO$_2$; or pyridyl optionally substituted by halogen or haloalkyl; or —CH$_2$R$^7$ wherein R$^7$ is phenyl optionally substituted by halogen, alkyl or alkoxy; or —CH$_2$CH$_2$R$^7$ wherein R$^7$ is phenyl;
Q is a group (A1) wherein:
W is CR$^6$; R$^3$ is hydrogen or halogen; R$^6$ is halogen; R$^4$ is hydrogen; and R$^5$ is halogen, CF$_3$ or OCF$_3$; or wherein:
W is CR$^6$; R$^3$ is hydrogen; R$^6$ is halogen; R$^4$ is CF$_3$; and R$^5$ is hydrogen; and R$^2$ is —NHR$^{13}$ or —N=CH(R$^{14}$); wherein R$^{13}$ is hydrogen or alkyl; and R$^{14}$ is alkoxy.

Methods or Processes of Synthesis

The compounds of general formula (I) can be prepared by the application or adaptation of known methods (i.e. methods heretofore used or described in the chemical literature).

Compounds of general formula (I) wherein R$^1$, R$^2$ and Q are defined above and n is zero may be prepared by the reaction of a compound of formula (II):

(II)

wherein R$^2$ and Q are defined above, with a thiol of formula (III):

R$^1$SH          (III)

wherein R$^1$ is as defined above, in the presence of a Lewis acid, preferably boron trifluoride etherate, to give a hemithioacetal intermediate of formula (IV):

(IV)

which is not generally isolated, and is treated in situ with a reducing agent generally a hydrosilane derivative (i.e. a silane which contains one or more hydrogen atoms), preferably a trialkylsilane such as triethylsilane. The reaction is generally performed in a chlorinated solvent such as 1,2-dichloroethane, at a temperature of from 0° to 60° C.

Compounds of general formula (I) wherein $R^1$, $R^2$ and Q are defined above, and n is 1 or 2 may be prepared by oxidizing a corresponding compound in which n is 0 or 1. The oxidation is generally performed using a peracid such as 3-chloroperbenzoic acid in a solvent such as dichloromethane, or with hydrogen peroxide generally in the presence of trifluoroacetic acid, at a temperature of from 0° C. to the reflux temperature of the solvent.

These processes are also an object of the invention.

Compounds of general formula (I) wherein $R^1$, Q and n are as defined above, and $R^2$ is as defined above with the exclusion of amino, may be prepared from the corresponding compounds in which $R^2$ is amino by the application of known methods for example as described in European Patent Publication Numbers 0234119, 511845, 352944 and 295117.

If desired, a compound of formula (I) produced by any of the above process embodiments may be converted into an agriculturally acceptable salt thereof.

Intermediates of formula (II) wherein $R^2$ is amino are known or may be prepared by known methods, for example by the Vilsmeier formylation of compounds of formula (V):

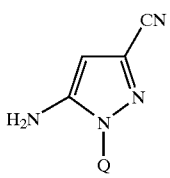

using phosphoryl chloride and N,N-dimethylformamide at a temperature of from 0° to 50° C. to give a compound of formula (VI):

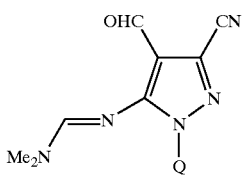

which is hydrolyzed, generally under acidic conditions, for example using hydrochloric acid, in a solvent such as tetrahydrofuran at a temperature of from 0° to 100° C.

Intermediates of formulas (III) and (V) are known or may be prepared by known methods.

The invention is illustrated by the following non-limiting examples, and in the tables it will be understood that 'Me' means methyl, 'Et' means ethyl, 'i-Pr' means isopropyl, 't-Bu' means tert butyl, and 'Ph' means phenyl.

EXAMPLE 1

2-Methylbutanethiol (0.327 mmol) was added to a solution of 1-(2,6-dichloro-4-trifluoromethylphenyl)-3-cyano-4-formyl pyrazole (0.297 mmol) in 1,2-dichloroethane. A solution of boron trifluoride etherate (2.0 ml of a 3.75% (v/v) solution in 1,2-dichloroethane), then triethylsilane (1.0 ml of a 7.08% (v/v) solution in 1,2-dichloroethane) was added and the mixture stirred at 20° C. overnight. The mixture was evaporated, redissolved in N,N-dimethylformamide and purified by LC/MS using a methanol/water gradient to give 5-amino-1-(2,6-dichloro-4-trifluoromethylphenyl)-3-cyano-4-(2-methylbutylthiomethyl)pyrazole (Compound 1, 0.15 mmol), MS 437.

By proceeding in a similar manner the following compounds of formula (I), shown in Table 1 in which $R^2$ is amino and n is zero were also prepared.

TABLE 1

| Cpd No. | R1 | Q | MS |
|---|---|---|---|
| 2 | methyl | 2,6-$Cl_2$-4-$CF_3$ Ph | 381 |
| 3 | cyclopentyl | 2,6-$Cl_2$-4-$CF_3$ Ph | 435 |
| 4 | cyclohexyl | 2,6-$Cl_2$-4-$CF_3$ Ph | 449 |
| 5 | 1,1-$Me_2$-propyl | 2,6-$Cl_2$-4-$CF_3$ Ph | 437 |
| 6 | isopropyl | 2,6-$Cl_2$-4-$CF_3$ Ph | 409 |
| 7 | 1-Me-propyl | 2,6-$Cl_2$-4-$CF_3$ Ph | 423 |
| 8 | benzyl | 2,6-$Cl_2$-4-$CF_3$ Ph | 457 |
| 9 | 3-Me-butyl | 2,6-$Cl_2$-4-$CF_3$ Ph | 437 |
| 10 | 4-Cl benzyl | 2,6-$Cl_2$-4-$CF_3$ Ph | 491 |
| 11 | 4-OMe benzyl | 2,6-$Cl_2$-4-$CF_3$ Ph | 487 |
| 12 | 2-Me-propyl | 2,6-$Cl_2$-4-$CF_3$ Ph | 423 |
| 13 | ethyl | 2,6-$Cl_2$-4-$CF_3$ Ph | 395 |
| 14 | propyl | 2,6-$Cl_2$-4-$CF_3$ Ph | 409 |
| 15 | 3-Cl-propyl | 2,6-$Cl_2$-4-$CF_3$ Ph | 443 |
| 16 | butyl | 2,6-$Cl_2$-4-$CF_3$ Ph | 423 |
| 17 | pentyl | 2,6-$Cl_2$-4-$CF_3$ Ph | 437 |
| 18 | 4-Me benzyl | 2,6-$Cl_2$-4-$CF_3$ Ph | 471 |
| 19 | 4-t-butyl benzyl | 2,6-$Cl_2$-4-$CF_3$ Ph | 513 |
| 20 | $CH_2CF_3$ | 2,6-$Cl_2$-4-$CF_3$ Ph | 449 |
| 21 | $CH_2CHCl_2$ | 2,6-$Cl_2$-4-$CF_3$ Ph | 464 |
| 22 | 2-naphthyl | 2,6-$Cl_2$-4-$CF_3$ Ph | 493 |
| 23 | Ph | 2,6-$Cl_2$-4-$CF_3$ Ph | 443 |
| 24 | 2,5-$Cl_2$ Ph | 2,6-$Cl_2$-4-$CF_3$ Ph | 512 |
| 25 | 2-OMe Ph | 2,6-$Cl_2$-4-$CF_3$ Ph | 473 |
| 26 | 2-i-Pr Ph | 2,6-$Cl_2$-4-$CF_3$ Ph | 485 |
| 27 | 2-Me Ph | 2,6-$Cl_2$-4-$CF_3$ Ph | 457 |
| 28 | 3,4-$Cl_2$ Ph | 2,6-$Cl_2$-4-$CF_3$ Ph | 512 |
| 29 | 3-Me Ph | 2,6-$Cl_2$-4-$CF_3$ Ph | 457 |
| 30 | 4-Br Ph | 2,6-$Cl_2$-4-$CF_3$ Ph | 522 |
| 31 | 4-OMe Ph | 2,6-$Cl_2$-4-$CF_3$ Ph | 473 |
| 32 | 4-pyridyl | 2,6-$Cl_2$-4-$CF_3$ Ph | 444 |
| 33 | 4-$NO_2$ Ph | 2,6-$Cl_2$-4-$CF_3$ Ph | 488 |
| 34 | 4-t-butyl Ph | 2,6-$Cl_2$-4-$CF_3$ Ph | 499 |
| 35 | 3-$CF_3$ Ph | 2,6-$Cl_2$-4-$CF_3$ Ph | 511 |
| 36 | 4-$OCF_3$ Ph | 2,6-$Cl_2$-4-$CF_3$ Ph | 527 |
| 37 | 2-$OCF_3$ Ph | 2,6-$Cl_2$-4-$CF_3$ Ph | 527 |
| 38 | 3,4-$(OMe)_2$ Ph | 2,6-$Cl_2$-4-$CF_3$ Ph | 503 |
| 39 | 2,4,6-$Cl_3$ Ph | 2,6-$Cl_2$-4-$CF_3$ Ph | 546 |
| 40 | 3-Cl-5-$CF_3$-pyrid-2-yl | 2,6-$Cl_2$-4-$CF_3$ Ph | 546 |
| 41 | cyclopentyl | 2,6-$Cl_2$-4-$OCF_3$ Ph | 451 |
| 42 | cyclohexyl | 2,6-$Cl_2$-4-$OCF_3$ Ph | 465 |
| 43 | 1,1-$Me_2$-propyl | 2,6-$Cl_2$-4-$OCF_3$ Ph | 453 |
| 44 | isopropyl | 2,6-$Cl_2$-4-$OCF_3$ Ph | 425 |
| 45 | 1-Me-propyl | 2,6-$Cl_2$-4-$OCF_3$ Ph | 439 |
| 46 | 3-Me-butyl | 2,6-$Cl_2$-4-$OCF_3$ Ph | 453 |
| 47 | 4-Cl benzyl | 2,6-$Cl_2$-4-$OCF_3$ Ph | 507 |
| 48 | 4-OMe benzyl | 2,6-$Cl_2$-4-$OCF_3$ Ph | 503 |
| 49 | 2-Me-propyl | 2,6-$Cl_2$-4-$OCF_3$ Ph | 439 |
| 50 | 2-Me-butyl | 2,6-$Cl_2$-4-$OCF_3$ Ph | 453 |
| 51 | ethyl | 2,6-$Cl_2$-4-$OCF_3$ Ph | 411 |
| 52 | propyl | 2,6-$Cl_2$-4-$OCF_3$ Ph | 425 |
| 53 | 3-Cl-propyl | 2,6-$Cl_2$-4-$OCF_3$ Ph | 459 |
| 54 | butyl | 2,6-$Cl_2$-4-$OCF_3$ Ph | 439 |
| 55 | 4-t-butyl benzyl | 2,6-$Cl_2$-4-$OCF_3$ Ph | 529 |
| 56 | $CH_2CF_3$ | 2,6-$Cl_2$-4-$OCF_3$ Ph | 465 |
| 57 | $CH_2CHCl_2$ | 2,6-$Cl_2$-4-$OCF_3$ Ph | 480 |
| 58 | 2-naphthyl | 2,6-$Cl_2$-4-$OCF_3$ Ph | 509 |
| 59 | Ph | 2,6-$Cl_2$-4-$OCF_3$ Ph | 459 |
| 60 | 2,5-$Cl_2$ Ph | 2,6-$Cl_2$-4-$OCF_3$ Ph | 528 |
| 61 | 2-OMe Ph | 2,6-$Cl_2$-4-$OCF_3$ Ph | 489 |
| 62 | 2-Me Ph | 2,6-$Cl_2$-4-$OCF_3$ Ph | 473 |
| 63 | 3,4-$Cl_2$ Ph | 2,6-$Cl_2$-4-$OCF_3$ Ph | 528 |
| 64 | 3-Me Ph | 2,6-$Cl_2$-4-$OCF_3$ Ph | 473 |
| 65 | 4-Br Ph | 2,6-$Cl_2$-4-$OCF_3$ Ph | 538 |
| 66 | 4-OMe Ph | 2,6-$Cl_2$-4-$OCF_3$ Ph | 489 |
| 67 | 4-pyridyl | 2,6-$Cl_2$-4-$OCF_3$ Ph | 460 |
| 68 | 4-$NO_2$ Ph | 2,6-$Cl_2$-4-$OCF_3$ Ph | 504 |
| 69 | 5-$NO_2$-pyrid-2-yl | 2,6-$Cl_2$-4-$OCF_3$ Ph | 505 |
| 70 | 3-$CF_3$ Ph | 2,6-$Cl_2$-4-$OCF_3$ Ph | 527 |
| 71 | 4-$OCF_3$ Ph | 2,6-$Cl_2$-4-$OCF_3$ Ph | 543 |
| 72 | 2-$OCF_3$ Ph | 2,6-$Cl_2$-4-$OCF_3$ Ph | 543 |
| 73 | 3,4-$(OMe)_2$ Ph | 2,6-$Cl_2$-4-$OCF_3$ Ph | 519 |
| 74 | 2,4,6-$Cl_3$ Ph | 2,6-$Cl_2$-4-$OCF_3$ Ph | 562 |

TABLE 1-continued

| Cpd No. | R1 | Q | MS |
|---|---|---|---|
| 75 | cyclopentyl | 2-Cl-4-CF$_3$ Ph | 400 |
| 76 | isopropyl | 2-Cl-4-CF$_3$ Ph | 374 |
| 77 | 2-Me-propyl | 2-Cl-4-CF$_3$ Ph | 388 |
| 78 | 3-Me-butyl | 2-Cl-4-CF$_3$ Ph | 402 |
| 79 | 4-Cl benzyl | 2-Cl-4-CF$_3$ Ph | 457 |
| 80 | 2-Me-propyl | 2-Cl-4-CF$_3$ Ph | 388 |
| 81 | 2-Me-butyl | 2-Cl-4-CF$_3$ Ph | 402 |
| 82 | decyl | 2-Cl-4-CF$_3$ Ph | 473 |
| 83 | ethyl | 2-Cl-4-CF$_3$ Ph | 360 |
| 84 | CH$_2$CH$_2$Ph | 2-Cl-4-CF$_3$ Ph | 436 |
| 85 | propyl | 2-Cl-4-CF$_3$ Ph | 374 |
| 86 | 3-Cl-propyl | 2-Cl-4-CF$_3$ Ph | 409 |
| 87 | butyl | 2-Cl-4-CF$_3$ Ph | 388 |
| 88 | 4-t-butyl benzyl | 2-Cl-4-CF$_3$ Ph | 478 |
| 89 | CH$_2$CF$_3$ | 2-Cl-4-CF$_3$ Ph | 414 |
| 90 | 2-naphthyl | 2-Cl-4-CF$_3$ Ph | 458 |
| 91 | Ph | 2-Cl-4-CF$_3$ Ph | 408 |
| 92 | 2,3,4,5,6-F$_5$ Ph | 2-Cl-4-CF$_3$ Ph | 498 |
| 93 | 2,5-Cl$_2$ Ph | 2-Cl-4-CF$_3$ Ph | 477 |
| 94 | 2-OMe Ph | 2-Cl-4-CF$_3$ Ph | 438 |
| 95 | 2-i-Pr Ph | 2-Cl-4-CF$_3$ Ph | 450 |
| 96 | 2-Me Ph | 2-Cl-4-CF$_3$ Ph | 422 |
| 97 | 3,4-Cl$_2$ Ph | 2-Cl-4-CF$_3$ Ph | 477 |
| 98 | 3-Me Ph | 2-Cl-4-CF$_3$ Ph | 422 |
| 99 | 4-Br Ph | 2-Cl-4-CF$_3$ Ph | 487 |
| 100 | 4-OMe Ph | 2-Cl-4-CF$_3$ Ph | 438 |
| 101 | 4-pyridyl | 2-Cl-4-CF$_3$ Ph | 409 |
| 102 | 4-t-butyl Ph | 2-Cl-4-CF$_3$ Ph | 464 |
| 103 | 3-CF$_3$ Ph | 2-Cl-4-CF$_3$ Ph | 476 |
| 104 | 4-i-Pr Ph | 2-Cl-4-CF$_3$ Ph | 450 |
| 105 | 4-OCF$_3$ Ph | 2-Cl-4-CF$_3$ Ph | 492 |
| 106 | 2-OCF$_3$ Ph | 2-Cl-4-CF$_3$ Ph | 492 |
| 107 | 3,4-(OMe)$_2$ Ph | 2-Cl-4-CF$_3$ Ph | 468 |
| 108 | 2,4,6-Cl$_3$ Ph | 2-Cl-4-CF$_3$ Ph | 512 |
| 109 | cyclohexyl | 2-Cl-5-CF$_3$ Ph | 414 |
| 110 | isopropyl | 2-Cl-5-CF$_3$ Ph | 374 |
| 111 | 2-Me-propyl | 2-Cl-5-CF$_3$ Ph | 388 |
| 112 | 4-Cl benzyl | 2-Cl-5-CF$_3$ Ph | 457 |
| 113 | propyl | 2-Cl-5-CF$_3$ Ph | 374 |
| 114 | pentyl | 2-Cl-5-CF$_3$ Ph | 402 |
| 115 | CH$_2$CF$_3$ | 2-Cl-5-CF$_3$ Ph | 414 |
| 116 | 2,3,4,5,6-F$_5$ Ph | 2-Cl-5-CF$_3$ Ph | 498 |
| 117 | 2,5-Cl$_2$ Ph | 2-Cl-5-CF$_3$ Ph | 477 |
| 118 | 2-OMe Ph | 2-Cl-5-CF$_3$ Ph | 438 |
| 119 | 2-i-Pr Ph | 2-Cl-5-CF$_3$ Ph | 450 |
| 120 | 3,4-Cl$_2$ Ph | 2-Cl-5-CF$_3$ Ph | 477 |
| 121 | 3-Me Ph | 2-Cl-5-CF$_3$ Ph | 422 |
| 122 | 4-Br Ph | 2-Cl-5-CF$_3$ Ph | 487 |
| 123 | 4-OMe Ph | 2-Cl-5-CF$_3$ Ph | 438 |
| 124 | 4-pyridyl | 2-Cl-5-CF$_3$ Ph | 409 |
| 125 | 4-NO$_2$ Ph | 2-Cl-5-CF$_3$ Ph | 453 |
| 126 | 4-t-butyl Ph | 2-Cl-5-CF$_3$ Ph | 464 |
| 127 | 3-CF$_3$ Ph | 2-Cl-5-CF$_3$ Ph | 476 |
| 128 | 4-OCF$_3$ Ph | 2-Cl-5-CF$_3$ Ph | 492 |
| 129 | 2-OCF$_3$ Ph | 2-Cl-5-CF$_3$ Ph | 492 |
| 130 | 3,4-(OMe)$_2$ Ph | 2-Cl-5-CF$_3$ Ph | 468 |
| 131 | cyclohexyl | 2,4,6-Cl$_3$ Ph | 415 |
| 132 | isopropyl | 2,4,6-Cl$_3$ Ph | 375 |
| 133 | benzyl | 2,4,6-Cl$_3$ Ph | 423 |
| 134 | 4-Cl benzyl | 2,4,6-Cl$_3$ Ph | 458 |
| 135 | 2-Me-butyl | 2,4,6-Cl$_3$ Ph | 403 |
| 136 | ethyl | 2,4,6-Cl$_3$ Ph | 361 |
| 137 | propyl | 2,4,6-Cl$_3$ Ph | 375 |
| 138 | pentyl | 2,4,6-Cl$_3$ Ph | 403 |
| 139 | hexyl | 2,4,6-Cl$_3$ Ph | 417 |
| 140 | CH$_2$CF$_3$ | 2,4,6-Cl$_3$ Ph | 415 |
| 141 | CH$_2$CHCl$_2$ | 2,4,6-Cl$_3$ Ph | 430 |
| 142 | 2-naphthyl | 2,4,6-Cl$_3$ Ph | 459 |
| 143 | 2-OMe Ph | 2,4,6-Cl$_3$ Ph | 439 |
| 144 | 2-iPr Ph | 2,4,6-Cl$_3$ Ph | 451 |
| 145 | 3,4-Cl$_2$ Ph | 2,4,6-Cl$_3$ Ph | 478 |
| 146 | 4-Br Ph | 2,4,6-Cl$_3$ Ph | 488 |
| 147 | 4-OMe Ph | 2,4,6-Cl$_3$ Ph | 439 |
| 148 | 4-OCF$_3$ Ph | 2,4,6-Cl$_3$ Ph | 493 |
| 149 | isopropyl | 2-Br-4,6-Cl$_2$ Ph | 420 |
| 150 | 3-Me-butyl | 2-Br-4,6-Cl$_2$ Ph | 448 |
| 151 | 4-Cl benzyl | 2-Br-4,6-Cl$_2$ Ph | 502 |

TABLE 1-continued

| Cpd No. | R1 | Q | MS |
|---|---|---|---|
| 152 | 2-Me-butyl | 2-Br-4,6-Cl$_2$ Ph | 448 |
| 153 | ethyl | 2-Br-4,6-Cl$_2$ Ph | 406 |
| 154 | CH$_2$CH$_2$Ph | 2-Br-4,6-Cl$_2$ Ph | 482 |
| 155 | propyl | 2-Br-4,6-Cl$_2$ Ph | 420 |
| 156 | 3-Cl-propyl | 2-Br-4,6-Cl$_2$ Ph | 454 |
| 157 | CH$_2$CF$_3$ | 2-Br-4,6-Cl$_2$ Ph | 460 |
| 158 | 2-naphthyl | 2-Br-4,6-Cl$_2$ Ph | 504 |
| 159 | Ph | 2-Br-4,6-Cl$_2$ Ph | 454 |
| 160 | 2,5-Cl$_2$ Ph | 2-Br-4,6-Cl$_2$ Ph | 523 |
| 161 | 2-iPr Ph | 2-Br-4,6-Cl$_2$ Ph | 496 |
| 162 | 2-Me Ph | 2-Br-4,6-Cl$_2$ Ph | 468 |
| 163 | 3,4-Cl$_2$ Ph | 2-Br-4,6-Cl$_2$ Ph | 523 |
| 164 | 3-Me Ph | 2-Br-4,6-Cl$_2$ Ph | 468 |
| 165 | 4-Br Ph | 2-Br-4,6-Cl$_2$ Ph | 533 |
| 166 | 4-OMe Ph | 2-Br-4,6-Cl$_2$ Ph | 484 |
| 167 | 4-t-butyl Ph | 2-Br-4,6-Cl$_2$ Ph | 510 |
| 168 | 4-OCF$_3$ Ph | 2-Br-4,6-Cl$_2$ Ph | 538 |
| 169 | 2,4,6-Cl$_3$ Ph | 2-Br-4,6-Cl$_2$ Ph | 557 |
| 170 | cyclopentyl | 2,6-Cl$_2$-4-Br Ph | 446 |
| 171 | cyclohexyl | 2,6-Cl$_2$-4-Br Ph | 460 |
| 172 | 1,1-Me$_2$-propyl | 2,6-Cl$_2$-4-Br Ph | 448 |
| 173 | isopropyl | 2,6-Cl$_2$-4-Br Ph | 420 |
| 174 | 1-Me-propyl | 2,6-Cl$_2$-4-Br Ph | 434 |
| 175 | 3-Me-butyl | 2,6-Cl$_2$-4-Br Ph | 448 |
| 176 | 4-Cl benzyl | 2,6-Cl$_2$-4-Br Ph | 502 |
| 177 | 4-OMe benzyl | 2,6-Cl$_2$-4-Br Ph | 498 |
| 178 | 2-Me-butyl | 2,6-Cl$_2$-4-Br Ph | 448 |
| 179 | ethyl | 2,6-Cl$_2$-4-Br Ph | 406 |
| 180 | propyl | 2,6-Cl$_2$-4-Br Ph | 420 |
| 181 | butyl | 2,6-Cl$_2$-4-Br Ph | 434 |
| 182 | hexyl | 2,6-Cl$_2$-4-Br Ph | 462 |
| 183 | CH$_2$CF$_3$ | 2,6-Cl$_2$-4-Br Ph | 460 |
| 184 | CH$_2$CHCl$_2$ | 2,6-Cl$_2$-4-Br Ph | 475 |

EXAMPLE 2

A solution of 5-amino-1-(2,6-dichloro-4-trifluoromethylphenyl)-3-cyano-4-methylpyrazole (1.0 g) in methanol was cooled to 0° C., then treated with sulfuric acid/isopropanol catalyst (1 ml), followed by hydrogen peroxide (0.31 g of 0% w/w). The mixture was stirred overnight, quenched with water, the solid collected and washed with methyl t-butyl ether to give 5-amino-1-(2,6-dichloro-4-trifluoromethylphenyl)-3-cyano-4-methylsulfinylmethylpyrazole (Compound 185, 0.63 g), MS 396. 1-(2,6-Dichloro4-trifluoromethylphenyl)-3-cyano-5-methylamino4-methylsulfinylmethylpyrazole (Compound 268) was prepared in a similar manner.

The following compounds of formula (I), shown in Table 2 in which R$^2$ is amino and n is 1 were prepared in a similar manner but replacing the methanol with trifluroacetic acid and without the sulfuric acid/isopropanol catalyst, and purified by silica gel chromatography using a heptane/ethyl acetate/methanol gradient.

TABLE 2

| Cpd No. | R1 | Q | MS |
|---|---|---|---|
| 186 | cyclopentyl | 2,6-Cl$_2$-4-CF$_3$ Ph | 451 |
| 187 | cyclohexyl | 2,6-Cl$_2$-4-CF$_3$ Ph | 465 |
| 188 | 1,1-Me$_2$-propyl | 2,6-Cl$_2$-4-CF$_3$ Ph | 453 |
| 189 | isopropyl | 2,6-Cl$_2$-4-CF$_3$ Ph | 425 |
| 190 | 1-Me-propyl | 2,6-Cl$_2$-4-CF$_3$ Ph | 439 |
| 191 | benzyl | 2,6-Cl$_2$-4-CF$_3$ Ph | 473 |
| 192 | 3-Me-butyl | 2,6-Cl$_2$-4-CF$_3$ Ph | 453 |
| 193 | 4-OMe benzyl | 2,6-Cl$_2$-4-CF$_3$ Ph | 503 |
| 194 | 2-Me-propyl | 2,6-Cl$_2$-4-CF$_3$ Ph | 439 |
| 195 | 2-Me-butyl | 2,6-Cl$_2$-4-CF$_3$ Ph | 453 |

TABLE 2-continued

| Cpd No. | R1 | Q | MS |
| --- | --- | --- | --- |
| 196 | ethyl | 2,6-Cl$_2$-4-CF$_3$ Ph | 411 |
| 197 | propyl | 2,6-Cl$_2$-4-CF$_3$ Ph | 425 |
| 198 | hexyl | 2,6-Cl$_2$-4-CF$_3$ Ph | 467 |
| 199 | 4-t-Bu benzyl | 2,6-Cl$_2$-4-CF$_3$ Ph | 529 |
| 200 | isopropyl | 2,6-Cl$_2$-4-OCF$_3$ Ph | 441 |
| 201 | 1-Me-propyl | 2,6-Cl$_2$-4-OCF$_3$ Ph | 455 |
| 202 | benzyl | 2,6-Cl$_2$-4-OCF$_3$ Ph | 489 |
| 203 | 4-OMe benzyl | 2,6-Cl$_2$-4-OCF$_3$ Ph | 519 |
| 204 | 2-Me-propyl | 2,6-Cl$_2$-4-OCF$_3$ Ph | 455 |
| 205 | 2-Me-butyl | 2,6-Cl$_2$-4-OCF$_3$ Ph | 469 |
| 206 | ethyl | 2,6-Cl$_2$-4-OCF$_3$ Ph | 427 |
| 207 | propyl | 2,6-Cl$_2$-4-OCF$_3$ Ph | 441 |
| 208 | cyclopentyl | 2-Cl-4-CF$_3$ Ph | 416 |
| 209 | 4-Cl benzyl | 2-Cl-4-CF$_3$ Ph | 473 |
| 210 | propyl | 2-Cl-4-CF$_3$ Ph | 390 |
| 211 | 4-Me benzyl | 2-Cl-4-CF$_3$ Ph | 452 |
| 212 | 4-t-Bu benzyl | 2-Cl-4-CF$_3$ Ph | 494 |
| 213 | benzyl | 2-Cl-5-CF$_3$ Ph | 438 |
| 214 | decyl | 2-Cl-5-CF$_3$ Ph | 489 |
| 215 | 4-Me benzyl | 2-Cl-5-CF$_3$ Ph | 452 |
| 216 | 2-OMe Ph | 2-Cl-5-CF$_3$ Ph | 454 |
| 217 | 3,4-Cl$_2$ Ph | 2-Cl-5-CF$_3$ Ph | (a) |
| 218 | 4-OCF$_3$ Ph | 2-Cl-5-CF$_3$ Ph | (a) |
| 219 | 3-Me-butyl | 2,4,6-Cl$_3$ Ph | 419 |
| 220 | ethyl | 2,4,6-Cl$_3$ Ph | 377 |
| 221 | butyl | 2,4,6-Cl$_3$ Ph | 405 |
| 222 | 4-t-Bu benzyl | 2,4,6-Cl$_3$ Ph | 495 |
| 223 | isopropyl | 2-Br-4,6-Cl$_2$ Ph | 436 |
| 224 | propyl | 2-Br-4,6-Cl$_2$ Ph | 436 |
| 225 | cyclohexyl | 2,6-Cl$_2$-4-Br Ph | 476 |
| 226 | 1,1-dimethylpropyl | 2,6-Cl$_2$-4-Br Ph | 464 |
| 227 | isopropyl | 2,6-Cl$_2$-4-Br Ph | 436 |
| 228 | 2-Me-propyl | 2,6-Cl$_2$-4-Br Ph | 450 |
| 229 | decyl | 2,6-Cl$_2$-4-Br Ph | 534 |
| 230 | propyl | 2,6-Cl$_2$-4-Br Ph | 436 |
| 231 | butyl | 2,6-Cl$_2$-4-Br Ph | 450 |

Note:
(a) = not observed.

By proceeding in a similar manner the following compounds of formula (I), shown in Table 2 in which $R^2$ is amino and n is 2, were also prepared.

TABLE 3

| Cpd No. | R1 | Q | MS |
| --- | --- | --- | --- |
| 232 | methyl | 2,6-Cl$_2$-4-CF$_3$ Ph | 413 |
| 233 | isopropyl | 2,6-Cl$_2$-4-CF$_3$ Ph | 441 |
| 234 | benzyl | 2,6-Cl$_2$-4-CF$_3$ Ph | (a) |
| 235 | ethyl | 2,6-Cl$_2$-4-CF$_3$ Ph | 427 |
| 236 | propyl | 2,6-Cl$_2$-4-CF$_3$ Ph | 441 |
| 237 | 3-Cl-propyl | 2,6-Cl$_2$-4-CF$_3$ Ph | 475 |
| 238 | butyl | 2,6-Cl$_2$-4-CF$_3$ Ph | 455 |
| 239 | hexyl | 2,6-Cl$_2$-4-CF$_3$ Ph | 483 |
| 240 | Ph | 2,6-Cl$_2$-4-CF$_3$ Ph | 475 |
| 241 | 4-OMe Ph | 2,6-Cl$_2$-4-CF$_3$ Ph | 505 |
| 242 | 4-tBu Ph | 2,6-Cl$_2$-4-CF$_3$ Ph | 531 |
| 243 | 3-CF$_3$ Ph | 2,6-Cl$_2$-4-CF$_3$ Ph | 543 |
| 244 | 4-iPr Ph | 2,6-Cl$_2$-4-CF$_3$ Ph | 517 |
| 245 | 4-OCF$_3$ Ph | 2,6-Cl$_2$-4-CF$_3$ Ph | 559 |
| 246 | 2-OCF$_3$ Ph | 2,6-Cl$_2$-4-CF$_3$ Ph | 559 |
| 247 | cyclopentyl | 2,6-Cl$_2$-4-OCF$_3$ Ph | 483 |
| 248 | benzyl | 2,6-Cl$_2$-4-OCF$_3$ Ph | 505 |
| 249 | 4-Cl benzyl | 2,6-Cl$_2$-4-OCF$_3$ Ph | 539 |
| 250 | 2-Me-propyl | 2,6-Cl$_2$-4-OCF$_3$ Ph | 471 |
| 251 | 2-Me-butyl | 2,6-Cl$_2$-4-OCF$_3$ Ph | 485 |
| 252 | decyl | 2,6-Cl$_2$-4-OCF$_3$ Ph | 555 |
| 253 | hexyl | 2,6-Cl$_2$-4-OCF$_3$ Ph | 499 |
| 254 | Ph | 2,6-Cl$_2$-4-OCF$_3$ Ph | 491 |
| 255 | 2-iPr Ph | 2,6-Cl$_2$-4-OCF$_3$ Ph | 533 |
| 256 | 3-Me-butyl | 2-Cl-4-CF$_3$ Ph | 434 |
| 257 | 4-t-Bu Ph | 2-Cl-4-CF$_3$ Ph | 496 |
| 258 | isopropyl | 2-Cl-5-CF$_3$ Ph | 406 |

TABLE 3-continued

| Cpd No. | R1 | Q | MS |
| --- | --- | --- | --- |
| 259 | 4-Cl benzyl | 2-Cl-5-CF$_3$ Ph | 489 |
| 260 | isopropyl | 2,4,6-Cl$_3$ Ph | 407 |
| 261 | 4-iPr Ph | 2-Br-4,6-Cl$_2$ Ph | 528 |
| 262 | 2-OCF$_3$ Ph | 2-Br-4,6-Cl$_2$ Ph | 570 |
| 263 | 4-Cl benzyl | 2,6-Cl$_2$-4-CF$_3$ Ph | 498 |
| 264 | propyl | 2,6-Cl$_2$-4-CF$_3$ Ph | 416 |
| 265 | propyl | 2-Br-4,6-Cl$_2$ Ph | 452 |
| 266 | CH$_2$CHCl$_2$ | 2,6-Cl$_2$-4-CF$_3$ Ph | (a) |
| 267 | 4-Cl benzyl | 2,6-Cl$_2$-4-Br Ph | 534 |

Note:
(a) = not observed.

EXAMPLE 3

Sodium borohydride (420 mg) was added portionwise to a solution of 1-(2,6-dichloro-4-trifluoromethylphenyl)-3-cyano-5-ethoxycarbonylamino-4-methylthiomethlpyrazole (854 mg) in methanol. The mixture was evaporated, diluted with dichloromethane and water, and the organic phase dried (magnesium sulfate) and evaporated to give 1-(2,6-dichloro-4-trifluoromethylphenyl)-3-cyano-5-methylamino-4-methylthiomethylpyrazole.

EXAMPLE 4

A solution of 5-amino-1-(2,6-dichloro-4-trifluoromethylphenyl)-3-cyano-4-methylthiomethylpyrazole (801 mg) in triethyl orthoformate was heated to 80° C., concentrated hydrochloric acid (2 drops) added, and the mixture heated until it had a pH of 6. Evaporation then gave 1-(2,6-dichloro-4-trifluromethylphenyl)-3-cyano-5-ethoxymethyleneamino-4-methylthiomethylpyrazole (Compound 269, 875 mg).

The term "compound of the invention" as used hereinafter embraces a compound of formula (I) as defined above and a pesticidally acceptable salt thereof.

One aspect of the present invention as defined above is a method for the control of pests at a locus. The locus includes, for example, the pest itself, the place (plant, field, forest, orchard, waterway, soil, plant product, or the like) where the pest resides or feeds, or a place susceptible to future infestation by the pest. The compound of the invention may therefore be applied directly to the pest, to the place where the pest resides or feeds, or to the place susceptible to future infestation by the pest.

As is evident from the foregoing pesticidal uses, the present invention provides pesticidally active compounds and methods of use of said compounds for the control of a number of pest species which includes: arthropods, especially insects or mites, or plant nematodes. The compound of the invention may thus be advantageously employed in practical uses, for example, in agricultural or horticultural crops, in forestry, in veterinary medicine or livestock husbandry, or in public health.

The compounds of the invention may be used for example in the following applications and on the following pests:

For the control of soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

In the protection of stored products, for example cereals, including grain or flour, groundnuts, animal feedstuffs, timber or household goods, e.g. carpets and textiles, compounds of the invention are useful against attack by arthropods, more especially beetles, including weevils, moths or mites, for example Ephestia spp. (flour moths), Anthrenus spp. (carpet beetles), Tribolium spp. (flour beetles), Sitophilus spp. (grain weevils) or Acarus spp. (mites).

In the control of cockroaches, ants or termites or similar arthropod pests in infested domestic or industrial premises or in the control of mosquito larvae in waterways, wells, reservoirs or other running or standing water.

For the treatment of foundations, structures or soil in the prevention of the attack on building by termites, for example, Reticulitermes spp., Heterotermes spp., Coptotermes spp.

In agriculture against adults, larvae and eggs of Lepidoptera (butterflies and moths), e.g. Heliothis spp. such as *Heliothis virescens* (tobacco budworm), *Heliothis armigera* and *Heliothis zea*. Against adults and larvae of Coleoptera (beetles) e.g. Anthonomus spp. e.g. grandis (cotton boll weevil), *Leptinotarsa decemlineata* (Colorado potato beetle), Diabrotica spp. (corn rootworms). Against Heteroptera (Hemiptera and Homoptera) e.g. Psylla spp., Bemisia spp., Trialeurodes spp., Aphis spp., Myzus spp., *Megoura viciae*, Phylloxera spp., Nephotettix spp. (rice leaf hoppers), Nilaparvata spp.

Against Diptera e.g. Musca spp. Against Thysanoptera such as *Thrips tabaci*. Against Orthoptera such as Locusta and Schistocerca spp., (locusts and crickets) e.g. Gryllus spp., and Acheta spp. for example, *Blatta orientalis, Periplaneta americana, Blatella germanica, Locusta migratoria migratorioides,* and *Schistocerca gregaria*. Against Collembola e.g. Periplaneta spp. and Blatella spp. (roaches).

Against arthropods of agricultural significance such as Acari (mites) e.g. Tetranychus spp., and Panonychus spp.

Against nematodes which attack plants or trees of importance to agriculture, forestry or horticulture either directly or by spreading bacterial, viral, mycoplasma or fungal diseases of the plants. For example root-knot nematodes such as Meloidogyne spp. (e.g. *M. incognita*).

In the field of veterinary medicine or livestock husbandry or in the maintenance of public health against arthropods which are parasitic internally or externally upon vertebrates, particularly warm-blooded vertebrates, for example domestic animals, e.g. cattle, sheep, goats, equines, swine, poultry, dogs or cats, for example Acarina, including ticks (e.g. Ixodes spp., Boophilus spp. e.g. *Boophilus microplus,* Rhipicephalus spp. e.g. *Rhipicephalus appendiculatus* Ornithodorus spp. (e.g. *Ornithodorus moubata*) and mites (e.g. Damalinia spp.); Diptera (e.g. Aedes spp., Anopheles spp., Musca spp., Hypoderma spp.); Hemiptera; Dictyoptera (e.g. Periplaneta spp., Blatella spp.); Hymenoptera; for example against infections of the gastro-intestinal tract caused by parasitic nematode worms, for example members of the family Trichostrongylidae.

In practical use for the control of arthropods, especially insects or mites, or nematode pests of plants, a method, for example, comprises applying to the plants or to the medium in which they grow a pesticidally effective amount of a compound of the invention. For such a method, the active compound is generally applied to the locus in which the arthropod or nematode infestation is to be controlled at an effective rate in the range of about 2 g to about 5 kg of the active compound per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. Preferably an effective rate range of the active compound is from about 10 g/ha to about 400 g/ha, more preferably from about 50 g/ha to about 200 g/ha.

When a pest is soil-borne, the active compound, generally in a formulated composition, is distributed evenly over the area to be treated (i.e., for example broadcast or band treatment) in any convenient manner and is applied at rates from about 10 g/ha to about 400 g ai/ha, preferably from about 50 g/ha to about 200 g ai/ha. When applied as a root dip to seedlings or drip irrigation to plants the liquid solution or suspension contains from about 0.075 to about 1000 mg ai/l, preferably from about 25 to about 200 mg ai/l. Application may be made, if desired, to the field or crop-growing area generally or in close proximity to the seed or plant to be protected from attack. The active component can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting.

Accordingly, in a further aspect of the invention there is provided a seed, treated or coated with a compound of the formula (I) or a composition as described hereinafter.

The compound of the invention and methods of control of pests therewith are of particular value in the protection of field, forage, plantation, glasshouse, orchard or vineyard crops, of ornamentals, or of plantation or forest trees, for example: cereals (such as wheat or rice), cotton, vegetables (such as peppers), field crops (such as sugar beets, soybeans or oil seed rape), grassland or forage crops (such as maize or sorghum), orchards or groves (such as of stone or pit fruit or citrus), ornamental plants, flowers or vegetables or shrubs under glass or in gardens or parks, or forest trees (both deciduous and evergreen) in forests, plantations or nurseries. They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compound of the invention and methods of use thereof are of particular value in the control of arthropods or helminths which are injurious to, or spread or act as vectors of diseases in domestic animals, for example those hereinbefore mentioned, and more especially in the control of ticks, mites, lice, fleas, midges, or biting, nuisance or myiasis flies. The compounds of the invention are particularly useful in controlling arthropods or helminths which are present inside domestic host animals or which feed in or on the skin or suck the blood of the animal, for which purpose they may be administered orally, parenterally, percutaneously or topically.

Accordingly, in a further aspect of the invention there is provided the use of a compound of the formula (I) or a composition hereinafter described for preparing a veterinary medicine and a verterinary medicine comprising said compound. The compositions hereinafter described for application to growing crops or crop growing loci or as a seed dressing may, in general, alternatively be employed in the protection of stored products, household goods, property or areas of the general environment. Suitable means of applying the compounds of the invention include: to growing crops as foliar sprays (for example as an in-furrow spray), dusts, granules, fogs or foams or also as suspensions of finely divided or encapsulated compositions as soil or root treatments by liquid drenches, dusts, granules, smokes or foams; to seeds of crops via application as seed dressings by liquid slurries or dusts; to animals infested by or exposed to infestation by arthropods or helminths, by parenteral, oral or topical application of compositions in which the active ingredient exhibits an immediate and/or prolonged action over a period of time against the arthropods or helminths, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems; to the environment in general or to specific locations where pests may lurk, including stored products, timber, household goods, or domestic or industrial premises, as sprays, fogs, dusts, smokes, wax-smears, lacquers, granules or baits, or in tricklefeeds to waterways, wells, reservoirs or other running or standing water.

According to a further feature of the present invention there is provided a pesticidal composition comprising one or more compounds of the invention as defined above, in a pesticidally effective amount, in association with, and preferably homogeneously dispersed in one or more compatible agriculturally acceptable diluents or carriers and/or surface active agents (i.e., diluents or carriers and/or surface active agents of the type generally accepted in the art as being suitable for use in herbicidal compositions and which are compatible with compounds of the invention).

In practice, the compounds of the invention most frequently form parts of compositions. These compositions can be employed to control arthropods, especially insects, or plant nematodes or mites. The compositions may be of any type known in the art suitable for application to the desired pest in any premises or indoor or outdoor area. These compositions contain at least one compound of the invention as the active ingredient, in a pesticidally effective amount, in combination or association with one or more other compatible components which are for example, solid or liquid carriers or diluents, adjuvants, surface-active agents, or the like appropriate for the intended use and which are agronomically or medicinally acceptable. These compositions, which may be prepared by any manner known in the art, likewise form a part of this invention.

These compositions may also contain other kinds of ingredients such as protective colloids, adhesives, thickeners, thixotropic agents, penetrating agents, spray oils (especially for acaridical use), stabilizers, preservative agents (especially mold preservatives), sequestering agents, or the like, as well as other known active ingredients with pesticidal properties (particularly insecticidal, miticidal, nematicidal, or fungicidal) or with properties regulating the growth of plants. More generally, the compounds employed in the invention may be combined with all the solid or liquid additives corresponding to the usual techniques of formulation.

Examples of other pesticidally-active compounds which may be included in, or used in conjunction with the compositions of the present invention are: acephate, chlorpyrifos, demeton-S-methyl, disulfoton, ethoprofos, fenitrothion, fenamiphos, fonofos, isazophos, isofenphos, malathion, monocrotophos, parathion, phorate, phosalone, pirimiphos-methyl, terbufos, triazophos, cyfluthrin, cypermethrin, deltamethrin, fenpropathrin, fenvalerate, permethrin, tefluthrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectins, milbemycins, thiophanate, trichlorfon, dichlorvos, diaveridine or dimetriadazole.

Compositions, suitable for applications in agriculture, horticulture, or the like include formulations suitable for use as, for example, sprays, dusts, granules, fogs, foams, emulsions, or the like.

The effective use doses of the compounds employed in the invention can vary within wide limits, particularly depending on the nature of the pest to be eliminated or degree of infestation, for example, of crops with these pests. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates, especially aluminum or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or coloring agents which, when solid, may also serve as a diluent.

The carrier may also be liquid, for example: water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulfoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Among these are e.g., salts of polyacrylic acids, salts of lignosulfonic acids, salts of phenolsulfonic or naphthalenesulfonic acids, polycondensates of ethylene oxide with fatty alcohols or fatty acids or fatty esters or fatty amines, substituted phenols (particularly alkylphenols or arylphenols), salts of sulfosuccinic acid esters, taurine derivatives (particularly alkyltaurates), phosphoric esters of alcohols or of polycondensates of ethylene oxide with phenols, esters of fatty acids with polyols, or sulfate, sulfonate or phosphate functional derivatives of the above compounds. The presence of at least one surface-active agent is generally essential when the active ingredient and/or the inert carrier are only slightly water soluble or are not water soluble and the carrier agent of the composition for application is water.

Compositions of the invention may further contain other additives such as adhesives or colorants. Adhesives such as carboxymethylcellulose or natural or synthetic polymers in the form of powders, granules or lattices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc.

For their agricultural application, the compounds of the invention are therefore generally in the form of compositions, which are in various solid or liquid forms.

Solid forms of compositions which can be used are dusting powders (with a content of the compound of the invention ranging up to 80%), wettable powders or granules (including water dispersible granules), particularly those obtained by extrusion, compacting, impregnation of a granular carrier, or granulation starting from a powder (the content of the compound of the invention in these wettable powders or granules being between about 0.5 and about 80%). Solid homogenous or heterogenous compositions containing one or more compounds of the invention, for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications, be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (e.g., low or ultra-low volume) depending upon the need or application technique. The compound or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble. Some organic solids or inorganic salts may be dissolved in the carrier to help prevent settling or as antifreezes for water.

The wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient is thoroughly mixed in a suitable blender with additional substances which may be impregnated on the porous filler and is ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

The rates and concentrations of the formulated compositions may vary according to the method of application or the nature of the compositions or use thereof. Generally speaking, the compositions for application to control arthropod or plant nematode pests usually contain from about 0.00001% to about 95%, more particularly from about 0.0005% to about 50% by weight of one or more compounds of the invention, or of total active ingredients (that is to say the compounds of the invention, together with other substances toxic to arthropods or plant nematodes, synergists, trace elements or stabilizers). The actual compositions employed and their rate of application will be selected to achieve the desired effect(s) by the farmer, livestock producer, medical or veterinary practitioner, pest control operator or other person skilled in the art.

Solid or liquid compositions for application topically to animals, timber, stored products or household goods usually contain from about 0.00005% to about 90%, more particularly from about 0.001% to about 10%, by weight of one or more compounds of the invention. For administration to animals orally or parenterally, including percutaneously solid or liquid compositions, these normally contain from about 0.1% to about 90% by weight of one or more compounds of the invention. Medicated feedstuffs normally contain from about 0.001% to about 3% by weight of one or more compounds of the invention. Concentrates or supplements for mixing with feedstuffs normally contain from about 5% to about 90%, preferably from about 5% to about 50%, by weight of one or more compounds of the invention. Mineral salt licks normally contain from about 0.1% to about 10% by weight of one or more compounds of formula (I) or pesticidally acceptable salts thereof.

Dusts or liquid compositions for application to livestock, goods, premises or outdoor areas may contain from about 0.0001% to about 15%, more especially from about 0.005% to about 2.0%, by weight, of one or more compounds of the invention. Suitable concentrations in treated waters are between about 0.0001 ppm and about 20 ppm, more particularly about 0.001 ppm to about 5.0 ppm of one or more compounds of the invention, and may be used therapeutically in fish farming with appropriate exposure times. Edible baits may contain from about 0.01% to about 5%, preferably from about 0.01% to about 1.0%, by weight, of one or more compounds of the invention.

When administered to vertebrates parenterally, orally or by percutaneous or other means, the dosage of compounds of the invention, will depend upon the species, age, or health of the vertebrate and upon the nature and degree of its actual or potential infestation by arthropod or helminth pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition EXAMPLES 2A–2M illustrate compositions for use against arthropods, especially mites or insects, or plant nematodes, which comprise, as active ingredient, compounds of the invention, such as those described in the preparative examples. The compositions described in EXAMPLES 2A–2M can each be diluted to give a sprayable composition at concentrations suitable for use in the field. Generic chemical descriptions of the ingredients (for which all of the following percentages are in weight percent), used in the composition EXAMPLES 2A–2M exemplified below, are as follows:

| TRADE NAME | CHEMICAL DESCRIPTION |
|---|---|
| Ethylan BCP | Nonylphenol ethylene oxide condensate |
| Soprophor BSU | Tristyrylphenol ethylene oxide condensate |
| Arylan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan $NO_2$ | Sodium lignosulfonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

EXAMPLE 2A

A water soluble concentrate is prepared with the composition as follows:

| | |
|---|---|
| Active ingredient | 7% |
| Ethylan BCP | 10% |
| N-methylpyrrolidone | 83% |

To a solution of Ethylan BCP dissolved in a portion of N-methylpyrrolidone is added the active ingredient with heating and stirring until dissolved. The resulting solution is made up to volume with the remainder of the solvent.

EXAMPLE 2B

An emulsifiable concentrate (EC) is prepared with the composition as follows:

| | |
|---|---|
| Active ingredient | 25% (max) |
| Soprophor BSU | 10% |
| Arylan CA | 5% |
| N-methylpyrrolidone | 50% |
| Solvesso 150 | 10% |

The first three components are dissolved in N-methylpyrrolidone and to this is then added the Solvesso 150 to give the final volume.

EXAMPLE 2C

A wettable powder (WP) is prepared with the composition as follows:

| | |
|---|---|
| Active ingredient | 40% |
| Arylan S | 2% |
| Darvan NO$_2$ | 5% |
| Celite PF | 53% |

The ingredients are mixed and ground in a hammer-mill to a powder with a particle size of less than 50 microns.

EXAMPLE 2D

An aqueous-flowable formulation is prepared with the composition as follows:

| | |
|---|---|
| Active ingredient | 40.00% |
| Ethylan BCP | 1.00% |
| Sopropon T360 | 0.20% |
| Ethylene glycol | 5.00% |
| Rhodigel 230 | 0.15% |
| Water | 53.65% |

The ingredients are intimately mixed and are ground in a bead mill until a mean particle size of less than 3 microns is obtained.

EXAMPLE 2E

An emulsifiable suspension concentrate is prepared with the composition as follows:

| | |
|---|---|
| Active ingredient | 30.0% |
| Ethylan BCP | 10.0% |
| Bentone 38 | 0.5% |
| Solvesso 150 | 59.5% |

The ingredients are intimately mixed and ground in a beadmill until a mean particle size of less than 3 microns is obtained.

EXAMPLE 2F

A water dispersible granule is prepared with the composition as follows:

| | |
|---|---|
| Active ingredient | 30% |
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

EXAMPLE 2G

A dusting powder is prepared with the composition as follows:

| | |
|---|---|
| Active ingredient | 1 to 10% |
| Talc powder-superfine | 99 to 90% |

The ingredients are intimately mixed and further ground as necessary to achieve a fine powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

EXAMPLE 2H

An edible bait is prepared with the composition as follows:

| | |
|---|---|
| Active ingredient | 0.1 to 1.0% |
| Wheat flour | 80% |
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

EXAMPLE 2I

A solution formulation is prepared with a composition as follows:

| | |
|---|---|
| Active ingredient | 15% |
| Dimethyl sulfoxide | 85% |

The active ingredient is dissolved in dimethyl sulfoxide with mixing and/or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

EXAMPLE 2J

A wettable powder is prepared with the composition as follows:

| | |
|---|---|
| Active ingredient | 50% |
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example, dipterous larvae or plant nematodes, by spraying, or to domestic animals infested by, or at risk of infection by arthropods, by spraying or dipping, or by oral administration in drinking water, to control the arthropods.

EXAMPLE 2K

A slow release bolus composition is formed from granules containing the following components in varying percentages (similar to those described for the previous compositions) depending upon need:

Active ingredient

Density agent

Slow-release agent

Binder

The intimately mixed ingredients are formed into granules which are compressed into a bolus with a specific gravity of 2 or more. This can be administered orally to ruminant domestic animals for retention within the reticulorumen to give a continual slow release of active compound over an extended period of time to control infestation of the ruminant domestic animals by arthropods.

EXAMPLE 2L

A slow release composition in the form of granules, pellets, brickettes or the like can be prepared with compositions as follows:

Active ingredient 0.5 to 25%

Polyvinyl chloride 75 to 99.5%

Diotcyl phthalate (plasticizer)

The components are blended and then formed into suitable shapes by melt-extrusion or molding. These composition are useful, for example, for addition to standing water or for fabrication into collars or eartags for attachment to domestic animals to control pests by slow release.

EXAMPLE 2M

A water dispersible granule is prepared with the composition as follows:

| | |
|---|---|
| Active ingredient | 85% (max) |
| Polyvinylpyrrolidone | 5% |
| Attapulgite clay | 6% |
| Sodium lauryl sulfate | 2% |
| Glycerine | 2% |

The ingredients are mixed as a 45% slurry with water and wet milled to a particle size of 4 microns, then spray-dried to remove water.

Methods of Pesticidal Use

The following representative test procedures, using compounds of the invention, were conducted to determine the pesticidal use and activity of compounds of the invention against certain insects, including aphids and nematodes. The specific species tested were as follows:

Methods A: Systemic Aphid Screen

Untreated cotton seeds were planted in a sandy loam soil and grown until the cotyledons were fully expanded. About 25 cotton aphids (*Aphis gossypii*) were transferred to each plant and 24 hours later the soil was drenched with test solution in aqueous acetone (99:1 v/v) at various soil concentrations and the plants maintained in a growth chamber. Six days after treatment the number of living aphids was assessed relative to an untreated control and a rating given (1=70–99% of untreated control, 3=31–69%, 4=1–30%, 5=0 aphids on the plant), and the LC50 values calculated.

The following compounds gave a score of 3 or more at a concentration of 100 ppm or less, or had an LC50 of 100 ppm or less:

1, 2, 4–6, 8–10, 13, 15, 17–19, 21, 22, 24, 25, 28, 29, 31–33, 35–37, 41, 43, 50, 65, 67, 70, 80, 81, 84, 87, 88, 93–110, 113–119, 123, 126, 131, 133–135, 138, 139, 141, 144, 145, 147, 149, 150, 159, 161, 162, 164, 168, 171, 175, 182, 185, 186, 188, 240–243, 251, 252, 255 and 261–263.

Method B: Nematode Test

Infected roots of tomato plants, containing egg masses of Southern root-knot nematode (*Meloidogyne incognita*), were removed from a stock culture and cleaned of soil, and the nematode eggs separated from the root tissue and rinsed with water. Samples of the egg suspension were placed on a fine screen over a receiving bowl, in which the water level was adjusted to be in contact with the screen. From the bowl, juveniles were collected on a fine screen.

Soil having 0–1% moisture content was placed in a cup. A stock solution of the test compounds in dimethylsulfoxide was prepared and diluted with water and the solutions thus obtained were applied to the soil at the rates of 250, 500 and 1000 g/ha. After 12–24 hours cucumber seeds were added and the soil and seeds mixed. An aqueous suspension of *Meloidogyne incognita* of approximately 300 second stage juveniles (J2) or approximately 2500 eggs was added to the soil. The cup was covered with a vented lid and maintained at 27° C. and 80% relative humidity with a 14 hour photoperiod. Fourteen days later the roots were removed and evaluated for galling on a scale of 1, 3, 4 or 5 (1=severe galling, equal to the untreated control; 3=light galling; 4=very light galling; 5=no galling, complete control). Compounds scoring 3 or more were retested at multiple doses to give an ED3 value (effective dose to provide a 3 gall rating). The following compounds gave a score of 3 or more at a concentration of 1000 g/ha or less, or had an ED3 value of 1000 g/ha or less:

1, 2, 13, 14, 20, 36, 38, 42, 46, 50, 52, 56, 58, 63, 69, 78, 83–85, 92, 98, 103, 121, 137, 140, 143, 152, 154, 156, 158, 167, 172, 178, 181, 185, 196, 206, 220, 222, 250, 254, 257 and 258.

Method C: Aedes Aegyptii Test

Aqueous solution of Aedes aegyptii larvae were added to solutions containing known amounts of the test compounds in water containing <10% of dimethylsulfoxide and kept at 20° C. for 24 hours. The containers were tapped gently to stimulate the larval swimming response, and where little response to stimuli was observed the time since treatment was recorded. The ratings were 1=inactive, 3=moderately active, reduced swimming with 30–70% mortality, and 5=very active, little to no response to stimuli. The following compounds gave a score of 3 or more at a concentration of 100 ppm or less:

2–16, 20–25, 27, 28, 30–34, 36, 37, 39–41, 43–45, 47, 48, 51–54, 56, 57, 59, 62, 66, 69, 71, 73, 75–77, 83, 85, 86, 89, 91, 110–112, 118, 120, 122, 127–129, 132, 136, 137, 140, 141, 146, 149, 153, 155, 157, 166, 170, 173, 174, 176, 177, 179, 180, 183–185, 188–194, 196, 200, 206, 216, 233–235, 237, 238, 245 and 249.

Method D: Musca Domestica Test

Aqueous sugar solutions (40%) were added to samples of known amounts of test compounds in dimethylsulfoxide solutions. Four Musca domestica pupae were then added to each sample and kept until the flies had emerged. Each test sample was rated as follows: 1=0–1 flies dead, 3=2–3 flies dead, 5=4 flies dead. The following compounds gave a score of 3 or more:

2-4, 6, 12, 13, 20, 34, 37, 51, 76, 83, 106, 110, 112, 118, 125, 140, 141, 146, 149, 153, 185, 189, 194–197, 199, 200, 204, 206–215, 233 and 258.

Method E: Caenorhabdits Elegans Test

Aqueous solutions of mixed life stages of Caenorhabdits elegans (free living nematode) were added to solutions containing known amounts of the test compounds in water containing <1% of dimethylsulfoxide and kept at 20° C. for 6 or 7 days. Visual assessment was then made, rating the population size and behavior. The ratings were 1=inactive, large population increase and behavior similar to control; 3=moderately active, population as many or slightly more and slow motion; 4=active, population no to little increase and little movement; and 5=very active, population no increase and no or little motion. The following compounds gave a score of 3 or more at a concentration of 100 ppm or less:

5, 11, 15, 21–24, 28, 30, 33, 36, 39, 40, 43–45, 47, 48, 52–54, 56–66, 68–72, 74, 77, 79, 84–86, 89, 91, 97, 99, 103, 105, 106, 108, 112, 117, 120, 122, 125, 127–129, 142, 145, 146, 148, 151, 160, 163, 165, 168, 169, 176, 193–195, 198, 199, 201–203, 209, 217, 218, 236, 237, 245, 249, 259, 266 and 267.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound of the formula (I):

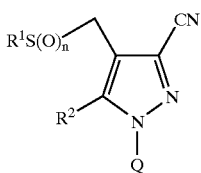

(I)

wherein:

Q is a group (A1) or (A2):

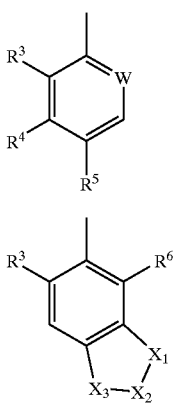

W is N or $CR^6$;

—$X_1$—$X_2$—$X_3$— is —$CF_2CF_2O$—, —$CF_2OCF_2$— or —$OCF_2O$—;

$R^1$ is alkyl, haloalkyl, alkenyl, haloalkenyl, alkynyl, haloalkynyl, cycloalkyl, cycloalkylalkyl or —$(CH_2)_mR^7$; or $R^1$ is naphthyl which is unsubstituted or is substituted by alkyl, haloalkyl, halogen, $NO_2$, alkoxy, haloalkoxy or $R^8S(O)_p$;

$R^2$ is hydrogen, halogen or unsubstituted or substituted amino;

$R^3$ and $R^6$ are each independently hydrogen or halogen;

$R^4$ is hydrogen or haloalkyl;

$R^5$ is hydrogen, halogen, haloalkyl, haloalkoxy, —$S(O)_pCF_3$ or $SF_5$;

$R^7$ is phenyl or a five to seven membered heteroaromatic ring having from one to four heteroatoms which are the same or different and are selected from the group consisting of nitrogen, oxygen and sulfur, which ring is unsubstituted or is substituted by $R^9$;

$R^8$ is alkyl or haloalkyl;

$R^9$ is alkyl, haloalkyl, halogen, CN, $NO_2$, $R^{10}O$, $R^8S(O)_p$, $C(O)R^8$, $C(O)OR^{10}$ or $NR^{10}R^{11}$; or when $R^7$ is phenyl two adjacent $R^9$ groups together form a —$CF_2OCF_2$— or —$OCF_2O$— group;

$R^{10}$ and $R^{11}$ are each independently hydrogen, alkyl or haloalkyl; and m, n and p each independently have the value zero, one or two;

or an agriculturally acceptable salt thereof.

2. A compound of the formula (I):

(I)

wherein:

Q is a group (A1) or (A2):

(A1)

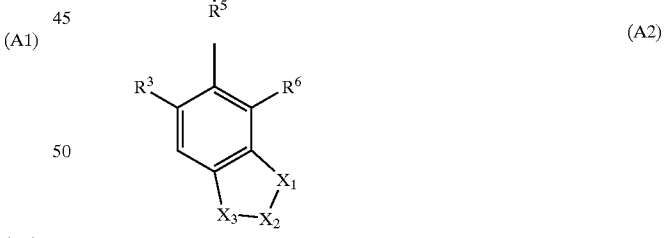

(A2)

W is N or $CR^6$;

—$X_1$—$X_2$—$X_3$— is —$CF_2CF_2O$—, —$CF_2OCF_2$— or —$OCF_2O$—;

$R^1$ is alkyl, haloalkyl, alkenyl, haloalkenyl, alkynyl, haloalkynyl, cycloalkyl, cycloalkylalkyl or —$(CH_2)_mR^7$; or $R^1$ is naphthyl which is unsubstituted or is substituted by alkyl, haloalkyl, halogen, $NO_2$, alkoxy, haloalkoxy or $R^8S(O)_p$;

$R^2$ is —$NR^{12}R^{13}$ or —$N=C(R^{10})(R^{14})$;

$R^3$ and $R^6$ are each independently hydrogen or halogen;

$R^4$ is hydrogen or haloalkyl;

$R^5$ is hydrogen, halogen, haloalkyl, haloalkoxy, —$S(O)_pCF_3$ or $SF_5$;

$R^7$ is phenyl or a five to seven membered heteroaromatic ring having from one to four heteroatoms which are the same or different and are selected from the group consisting of nitrogen, oxygen and sulfur, which ring is unsubstituted or is substituted by $R^9$;

$R^8$ is alkyl or haloalkyl;

$R^9$ is alkyl, haloalkyl, halogen, CN, $NO_2$, $R^{10}O$, $R^8S(O)_p$, $C(O)R^8$, $C(O)OR^{10}$ or $NR^{10}R^{11}$; or when $R^7$ is phenyl two adjacent $R^9$ groups together form a —$CF_2OCF_2$— or —$OCF_2O$— group;

$R^{10}$ and $R^{11}$ are each independently hydrogen, alkyl or haloalkyl;

m, n and p each independently have the value zero, one or two;

$R^{12}$ and $R^{13}$ are independently selected from the group consisting of hydrogen, alkyl, haloalkyl, alkenyl, haloalkenyl, alkynyl, haloalkynyl, —$C(O)R^{15}$ and $C(O)OR^{15}$; or $R^{12}$ and $R^{13}$ are joined together forming a divalent radical having 4 to 6 atoms in the chain, said divalent radical being alkylene, alkyleneoxyalkylene or alkyleneaminoalkylene;

$R^{14}$ is alkoxy or haloalkoxy; or $R^{14}$ is phenyl which is unsubstituted or is substituted by alkyl, haloalkyl, hydroxy, halogen, alkoxy, —$S(O)_pR^8$ or CN; and $R^{15}$ is alkenyl, haloalkenyl, alkynyl or haloalkynyl; or $R^{15}$ is alkyl which is unsubstituted or is substituted by halogen, alkoxy, $C(O)R^8$, $C(O)OR^{10}$, CN, —$S(O)_pR^8$, or $CONR^{10}R^{11}$;

or an agriculturally acceptable salt thereof.

3. A compound according to claim 1, wherein $R^1$ is alkyl, haloalkyl, cycloalkyl or naphthyl; or $R^1$ is phenyl which is unsubstituted or is substituted by halogen, alkyl, haloalkyl, alkoxy, haloalkoxy or $NO_2$; or $R^1$ is pyridyl which is unsubstituted or is substituted by halogen or haloalkyl; or $R^1$ is —$CH_2R^7$ wherein $R^7$ is phenyl which is unsubstituted or is substituted by halogen, alkyl or alkoxy; or $R^1$ is —$CH_2CH_2R^7$ wherein $R^7$ is phenyl.

4. A compound according to claim 2, wherein $R^1$ is alkyl, haloalkyl, cycloalkyl or naphthyl; or $R^1$ is phenyl which is unsubstituted or is substituted by halogen, alkyl, haloalkyl, alkoxy, haloalkoxy or $NO_2$; or $R^1$ is pyridyl which is unsubstituted or is substituted by halogen or haloalkyl; or $R^1$ is —$CH_2R^7$ wherein $R^7$ is phenyl which is unsubstituted or is substituted by halogen, alkyl or alkoxy; or $R^1$ is —$CH_2CH_2R^7$ wherein $R^7$ is phenyl.

5. A compound according to claim 1, wherein Q is a group (A1) wherein:

W is N or $CR^6$; $R^3$ and $R^6$ are each independently hydrogen or halogen; $R^4$ is hydrogen; and $R^5$ is halogen, $CF_3$, $OCF_3$ or $SF_5$; or wherein:

W is N or $CR^6$; $R^3$ and $R^6$ are each independently hydrogen or halogen; $R^4$ is $CF_3$; and $R^5$ is hydrogen.

6. A compound according to claim 2, wherein Q is a group (A1) wherein:

W is N or $CR^6$; $R^3$ and $R^6$ are each independently hydrogen or halogen; $R^4$ is hydrogen; and $R^5$ is halogen, $CF_3$, $OCF_3$ or $SF_5$; or wherein:

W is N or $CR^6$; $R^3$ and $R^6$ are each independently hydrogen or halogen; $R^4$ is $CF_3$; and $R^5$ is hydrogen.

7. A compound according to claim 3, wherein Q is a group (A1) wherein:

W is N or $CR^6$; $R^3$ and $R^6$ are each independently hydrogen or halogen; $R^4$ is hydrogen; and $R^5$ is halogen, $CF_3$, $OCF_3$ or $SF_5$; or wherein:

W is N or $CR^6$; $R^3$ and $R^6$ are each independently hydrogen or halogen; $R^4$ is $CF_3$; and $R^5$ is hydrogen.

8. A compound according to claim 4, wherein Q is a group A1) wherein:

W is N or $CR^6$; $R^3$ and $R^6$ are each independently hydrogen or halogen; $R^4$ is hydrogen; and $R^5$ is halogen, $CF_3$, $OCF_3$ or $SF_5$; or wherein:

W is N or $CR^6$; $R^3$ and $R^6$ are each independently hydrogen or halogen; $R^4$ is $CF_3$; and $R^5$ is hydrogen.

9. A compound according to claim 2, wherein $R^{12}$ is hydrogen, alkyl or —$C(O)R^{15}$; $R^{13}$ is hydrogen or alkyl; $R^{10}$ is hydrogen; $R^{14}$ is alkoxy; and $R^{15}$ is alkyl.

10. A compound according to claim 4, wherein $R^{12}$ is hydrogen, alkyl or —$C(O)R^{15}$; $R^{13}$ is hydrogen or alkyl; $R^{10}$ is hydrogen; $R^{14}$ is alkoxy; and $R^{15}$ is alkyl.

11. A compound according to claim 6, wherein $R^{12}$ is hydrogen, alkyl or —$C(O)R^{15}$; $R^{13}$ is hydrogen or alkyl; $R^{10}$ is hydrogen; $R^{14}$ is alkoxy; and $R^{15}$ is alkyl.

12. A compound according to claim 1, wherein n is 1 or 2.

13. A compound according to claim 2, wherein n is 1 or 2.

14. A compound according to claim 3, wherein n is 1 or 2.

15. A compound according to claim 4, wherein n is 1 or 2.

16. A compound according to claim 5, wherein n is 1 or 2.

17. A compound according to claim 5, wherein n is 1 or 2.

18. A compound according to claim 6, wherein n is 1 or 2.

19. A compound according to claim 7, wherein n is 1 or 2.

20. A compound of the formula (I):

(I)

wherein:

Q is a group (A1):

(A1)

W is N or $CR^6$;

$R^1$ is alkyl, haloalkyl, cycloalkyl or naphthyl; or $R^1$ is phenyl which is unsubstituted or is substituted by halogen, alkyl, haloalkyl, alkoxy, haloalkoxy or $NO_2$; or $R^1$ is pyridyl which is unsubstituted or is substituted by halogen or haloalkyl; or $R^1$ is —$CH_2R^7$ wherein $R^7$ is phenyl which is unsubstituted or is substituted by halogen, alkyl or alkoxy; or $R^1$ is —$CH_2CH_2R^7$ wherein $R^7$ is phenyl;

$R^2$ is $NR^{12}R^{13}$ or —$N=CHR^{14}$;

$R^3$ and $R^6$ are each independently hydrogen or halogen;

$R^4$ is hydrogen and $R^5$ is halogen, $CF_3$, $OCF_3$ or $SF_5$; or $R^4$ is $CF_3$ and $R^5$ is hydrogen;

$R^{12}$ is hydrogen, alkyl or —C(O)$R^{15}$;
$R^{13}$ is hydrogen or alkyl;
$R^{14}$ is alkoxy;
$R^{15}$ is alkyl; and
n is zero, one or two;
or an agriculturally acceptable salt thereof.

21. A compound of the formula (I):

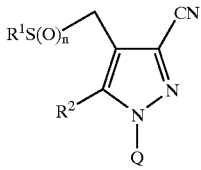
(I)

wherein:

Q is a group (A1):

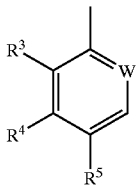
(A1)

W is N or $CR^6$;

$R^1$ is alkyl, haloalkyl, cycloalkyl or naphthyl; or $R^1$ is phenyl which is unsubstituted or is substituted by halogen, alkyl, haloalkyl, alkoxy, haloalkoxy or $NO_2$; or $R^1$ is pyridyl which is unsubstituted or is substituted by halogen or haloalkyl; or $R^1$ is —$CH_2R^7$ wherein $R^7$ is phenyl which is unsubstituted or is substituted by halogen, alkyl or alkoxy; or $R^1$ is —$CH_2CH_2R^7$ wherein $R^7$ is phenyl;

$R^2$ is $NR^{12}R^{13}$ or —N=$CHR^{14}$;

$R^3$ and $R^6$ are each independently hydrogen or halogen;

$R^4$ is hydrogen and $R^5$ is halogen, $CF_3$, $OCF_3$ or $SF_5$; or $R^4$ is $CF_3$ and $R^5$ is hydrogen;

$R^{12}$ is hydrogen, alkyl or —C(O)$R^{15}$;
$R^{13}$ is hydrogen or alkyl;
$R^{14}$ is alkoxy;
$R^{15}$ is alkyl; and
n is one or two;

or an agriculturally acceptable salt thereof.

22. A compound according to claim 21, wherein:

W is $CR^6$;

$R^1$ is alkyl, haloalkyl, cycloalkyl or naphthyl; or $R^1$ is phenyl which is unsubstituted or is substituted by halogen, alkyl, haloalkyl, alkoxy, haloalkoxy or $NO_2$; $R^1$ is —$CH_2R^7$ wherein $R^7$ is phenyl which is unsubstituted or is substituted by halogen, alkyl or alkoxy; or $R^1$ is —$CH_2CH_2R^7$ wherein $R^7$ is phenyl;

$R^2$ is $NR^{12}R^{13}$ or —N=$CHR^{14}$;

$R^3$ and $R^6$ are each independently hydrogen or halogen;

$R^4$ is hydrogen and $R^5$ is halogen, $CF_3$, $OCF_3$ or $SF_5$; or $R^4$ is $CF_3$ and $R^5$ is hydrogen;

$R^{12}$ is hydrogen, alkyl or —C(O)$R^{15}$;
$R^{13}$ is hydrogen or alkyl;
$R^{14}$ is alkoxy;
$R^{15}$ is alkyl; and
n is one or two;

or an agriculturally acceptable salt thereof.

23. A pesticidal composition comprising a pesticidally effective amount of a compound as claimed in claim 1 and at least one member selected from the group consisting of an agriculturally acceptable carrier and an agriculturally acceptable surface-active agent.

24. A pesticidal composition comprising a pesticidally effective amount of a compound as claimed in claim 2 and at least one member selected from the group consisting of an agriculturally acceptable carrier and an agriculturally acceptable surface-active agent.

25. A pesticidal composition comprising a pesticidally effective amount of a compound as claimed in claim 20 and at least one member selected from the group consisting of an agriculturally acceptable carrier and an agriculturally acceptable surface-active agent.

26. A pesticidal composition comprising a pesticidally effective amount of a compound as claimed in claim 21 and at least one member selected from the group consisting of an agriculturally acceptable carrier and an agriculturally acceptable surface-active agent.

27. A pesticidal composition comprising a pesticidally effective amount of a compound as claimed in claim 22 and at least one member selected from the group consisting of an agriculturally acceptable carrier and an agriculturally acceptable surface-active agent.

28. A method for the control of pests at a locus, said method comprising applying to said locus a pesticidally effective amount of a compound of the formula (I):

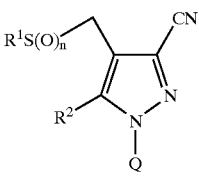
(I)

wherein:

Q is a group A1) or (A2):

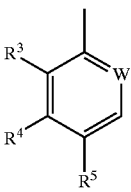
(A1)

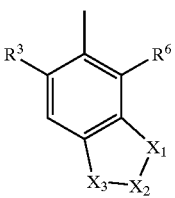
(A2)

W is N or $CR^6$;

—$X_1$—$X_2$—$X_3$— is —$CF_2CF_2O$—, —$CF_2OCF_2$— or —$OCF_2O$—;

$R^1$ is alkyl, haloalkyl, alkenyl, haloalkenyl, alkynyl, haloalkynyl, cycloalkyl, cycloalkylalkyl or —$(CH_2)_mR^7$; or $R^1$ is naphthyl which is unsubsti-

29 tuted or is substituted by alkyl, haloalkyl, halogen, NO$_2$, alkoxy, haloalkoxy or R$^8$S(O)$_p$;

R$^2$ is hydrogen, halogen or unsubstituted or substituted amino;

R$^3$ and R$^6$ are each independently hydrogen or halogen;

R$^4$ is hydrogen or haloalkyl;

R$^5$ is hydrogen, halogen, haloalkyl, haloalkoxy, —S(O)$_p$CF$_3$ or SF$_5$;

R$^7$ is phenyl or a five to seven membered heteroaromatic ring having from one to four heteroatoms which are the same or different and are selected from the group consisting of nitrogen, oxygen and sulfur, which ring is unsubstituted or is substituted by R$^9$;

R$^8$ is alkyl or haloalkyl;

R$^9$ is alkyl, haloalkyl, halogen, CN, NO$_2$, R$^{10}$O, R$^8$S(O)$_p$, C(O)R$^8$, C(O)OR$^{10}$ or NR$^{10}$R$^{11}$; or when R$^7$ is phenyl two adjacent R$^9$ groups together form a —CF$_2$OCF$_2$— or —OCF$_2$O— group;

R$^{10}$ and R$^{11}$ are each independently hydrogen, alkyl or haloalkyl; and m, n and p each independently have the value zero, one or two;

or an agriculturally acceptable salt thereof.

29. A method for the control of pests at a locus, said method comprising applying to said locus a pesticidally effective amount of a compound of the formula (I):

(I)

R$^1$S(O)$_n$ ... CN ... R$^2$ ... N ... Q wherein:

Q is a group (A1) or (A2):

(A1)

R$^3$ ... W ... R$^5$ (A2)

R$^3$ ... R$^6$ ... X$_1$ / X$_3$—X$_2$

W is N or CR$^6$;

—X$_1$—X$_2$—X$_3$— is —CF$_2$CF$_2$O—, —CF$_2$OCF$_2$— or —OCF$_2$O—;

R$^1$ is alkyl, haloalkyl, alkenyl, haloalkenyl, alkynyl, haloalkynyl, cycloalkyl, cycloalkylalkyl or —(CH$_2$)$_m$R$^7$; or R$^1$ is naphthyl which is unsubstituted or is substituted by alkyl, haloalkyl, halogen, NO$_2$, alkoxy, haloalkoxy or R$^8$S(O)$_p$;

R$^2$ is —NR$^{12}$R$^{13}$ or —N=C(R$^{10}$)(R$^{14}$);

R$^3$ and R$^6$ are each independently hydrogen or halogen;

R$^4$ is hydrogen or haloalkyl;

30

R$^5$ is hydrogen, halogen, haloalkyl, haloalkoxy, —S(O)$_p$CF$_3$ or SF$_5$;

R$^7$ is phenyl or a five to seven membered heteroaromatic ring having from one to four heteroatoms which are the same or different and are selected from the group consisting of nitrogen, oxygen and sulfur, which ring is unsubstituted or is substituted by R$^9$;

R$^8$ is alkyl or haloalkyl;

R$^9$ is alkyl, haloalkyl, halogen, CN, NO$_2$, R$^{10}$O, R$^8$S(O)$_p$, C(O)R$^8$, C(O)OR$^{10}$ or NR$^{10}$R$^{11}$; or when R$^7$ is phenyl two adjacent R$^9$ groups together form a —CF$_2$OCF$_2$— or —OCF$_2$O— group;

R$^{10}$ and R$^{11}$ are each independently hydrogen, alkyl or haloalkyl;

m, n and p each independently have the value zero, one or two;

R$^{12}$ and R$^{13}$ are independently selected from the group consisting of hydrogen, alkyl, haloalkyl, alkenyl, haloalkenyl, alkynyl, haloalkynyl, —C(O)R$^{15}$ and C(O)OR$^{15}$; or R$^{12}$ and R$^{13}$ are joined together forming a divalent radical having 4 to 6 atoms in the chain, said divalent radical being alkylene, alkyleneoxyalkylene or alkyleneaminoalkylene;

R$^{14}$ is alkoxy or haloalkoxy; or R$^{14}$ is phenyl which is unsubstituted or is substituted by alkyl, haloalkyl, hydroxy, halogen, alkoxy, —S(O)$_p$R$^8$ or CN; and R$^{15}$ is alkenyl, haloalkenyl, alkynyl or haloalkynyl; or R$^{15}$ is alkyl which is unsubstituted or is substituted by halogen, alkoxy, C(O)R$^8$, C(O)OR$^{10}$, CN, —S(O)$_p$R$^8$ or CONR$^{10}$R$^{11}$;

or an agriculturally acceptable salt thereof.

30. A method according to claim 28, wherein R$^1$ is alkyl, haloalkyl, cycloalkyl or naphthyl; or R$^1$ is phenyl which is unsubstituted or is substituted by halogen, alkyl, haloalkyl, alkoxy, haloalkoxy or NO$_2$; or R$^1$ is pyridyl which is unsubstituted or is substituted by halogen or haloalkyl; or R$^1$ is —CH$_2$R$^7$ wherein R$^7$ is phenyl which is unsubstituted or is substituted by halogen, alkyl or alkoxy; or R$^1$ is —CH$_2$CH$_2$R$^7$ wherein R$^7$ is phenyl.

31. A method according to claim 29, wherein R$^1$ is alkyl, haloalkyl, cycloalkyl or naphthyl; or R$^1$ is phenyl which is unsubstituted or is substituted by halogen, alkyl, haloalkyl, alkoxy, haloalkoxy or NO$_2$; or R$^1$ is pyridyl which is unsubstituted or is substituted by halogen or haloalkyl; or R$^1$ is —CH$_2$R$^7$ wherein R$^7$ is phenyl which is unsubstituted or is substituted by halogen, alkyl or alkoxy; or R$^1$ is —CH$_2$CH$_2$R$^7$ wherein R$^7$ is phenyl.

32. A method according to claim 28, wherein Q is a group A1) wherein:

W is N or CR$^6$; R$^3$ and R$^6$ are each independently hydrogen or halogen; R$^4$ is hydrogen; and R$^5$ is halogen, CF$_3$, OCF$_3$ or SF$_5$; or wherein:

W is N or CR$^6$; R$^3$ and R$^6$ are each independently hydrogen or halogen; R$^4$ is CF$_3$; and R$^5$ is hydrogen.

33. A method according to claim 29, wherein Q is a group (A1) wherein:

W is N or CR$^6$; R$^3$ and R$^6$ are each independently hydrogen or halogen; R$^4$ is hydrogen; and R$^5$ is halogen, CF$_3$, OCF$_3$ or SF$_5$; or wherein:

W is N or CR$^6$; R$^3$ and R$^6$ are each independently hydrogen or halogen; R$^4$ is CF$_3$; and R$^5$ is hydrogen.

34. A method according to claim 30, wherein Q is a group (A1) wherein:

W is N or CR$^6$; R$^3$ and R$^6$ are each independently hydrogen or halogen; R$^4$ is hydrogen; and R$^5$ is halogen, CF$_3$, OCF$_3$ or SF$_5$; or wherein:

W is N or CR$^6$; R$^3$ and R$^6$ are each independently hydrogen or halogen; R$^4$ is CF$_3$; and R$^5$ is hydrogen.

35. A method according to claim 31, wherein Q is a group (A1) wherein:
W is N or CR$^6$; R$^3$ and R$^6$ are each independently hydrogen or halogen; R$^4$ is hydrogen; and R$^5$ is halogen, CF$_3$, OCF$_3$ or SF$_5$; or wherein:
W is N or CR$^6$; R$^3$ and R$^6$ are each independently hydrogen or halogen; R$^4$ is CF$_3$; and R$^5$ is hydrogen.

36. A method according to claim 29, wherein R$^{12}$ is hydrogen, alkyl or —C(O)R$^{15}$; R$^{13}$ is hydrogen or alkyl; R$^{10}$ is hydrogen; R$^{14}$ is alkoxy; and R$^{15}$ is alkyl.

37. A method according to claim 31, wherein R$^{12}$ is hydrogen, alkyl or —C(O)R$^{15}$; R$^{13}$ is hydrogen or alkyl; R$^{10}$ is hydrogen; R$^{14}$ is alkoxy; and R$^{15}$ is alkyl.

38. A method according to claim 33, wherein R$^{12}$ is hydrogen, alkyl or —C(O)R$^{15}$; R$^{13}$ is hydrogen or alkyl; R$^{10}$ is hydrogen; R$^{14}$ is alkoxy; and R$^{15}$ is alkyl.

39. A method according to claim 28, wherein n is 1 or 2.
40. A method according to claim 29, wherein n is 1 or 2.
41. A method according to claim 30, wherein n is 1 or 2.
42. A method according to claim 31, wherein n is 1 or 2.
43. A method according to claim 32, wherein n is 1 or 2.
44. A method according to claim 33, wherein n is 1 or 2.
45. A method according to claim 34, wherein n is 1 or 2.
46. A method according to claim 35, wherein n is 1 or 2.

47. A method for the control of pests at a locus, said method comprising applying to said locus a pesticidally effective amount of a compound of the formula (I):

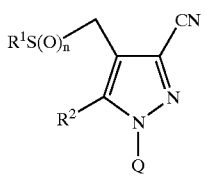

(I)

wherein:
Q is a group (A1):

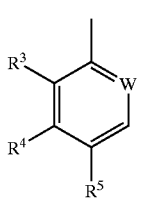

(A1)

W is N or CR$^6$;
R$^1$ is alkyl, haloalkyl, cycloalkyl or naphthyl; or R$^1$ is phenyl which is unsubstituted or is substituted by halogen, alkyl, haloalkyl, alkoxy, haloalkoxy or NO$_2$; or R$^1$ is pyridyl which is unsubstituted or is substituted by halogen or haloalkyl; or R$^1$ is —CH$_2$R$^7$ wherein R$^7$ is phenyl which is unsubstituted or is substituted by halogen, alkyl or alkoxy; or R$^1$ is —CH$_2$CH$_2$R$^7$ wherein R$^7$ is phenyl;
R$^2$ is NR$^{12}$R$^{13}$ or —N=CHR$^{14}$;
R$^3$ and R$^6$ are each independently hydrogen or halogen;
R$^4$ is hydrogen and R$^5$ is halogen, CF$_3$, OCF$_3$ or SF$_5$; or R$^4$ is CF$_3$ and R$^5$ is hydrogen;
R$^{12}$ is hydrogen, alkyl or —C(O)R$^{15}$;
R$^{13}$ is hydrogen or alkyl;
R$^{14}$ is alkoxy;
R$^{15}$ is alkyl; and
n is zero, one or two;
or an agriculturally acceptable salt thereof.

48. A method for the control of pests at a locus, said method comprising applying to said locus a pesticidally effective amount of a compound of the formula (I):

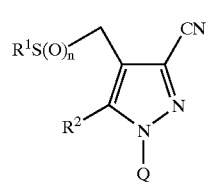

(I)

wherein:
Q is a group A1):

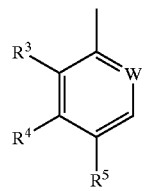

(A1)

W is N or CR$^6$;
R$^1$ is alkyl, haloalkyl, cycloalkyl or naphthyl; or R$^1$ is phenyl which is unsubstituted or is substituted by halogen, alkyl, haloalkyl, alkoxy, haloalkoxy or NO$_2$; or R$^1$ is pyridyl which is unsubstituted or is substituted by halogen or haloalkyl; or R$^1$ is —CH$_2$R$^7$ wherein R$^7$ is phenyl which is unsubstituted or is substituted by halogen, alkyl or alkoxy; or R$^1$ is —CH$_2$CH$_2$R$^7$ wherein R$^7$ is phenyl;
R$^2$ is NR$^{12}$R$^{13}$ or —N=CHR$^{14}$;
R$^3$ and R$^6$ are each independently hydrogen or halogen;
R$^4$ is hydrogen and R$^5$ is halogen, CF$_3$, OCF$_3$ or SF$_5$; or R$^4$ is CF$_3$ and R$^5$ is hydrogen;
R$^{12}$ is hydrogen, alkyl or —C(O)R$^{15}$;
R$^{13}$ is hydrogen or alkyl;
R$^{14}$ is alkoxy;
R$^{15}$ is alkyl; and
n is one or two;
or an agriculturally acceptable salt thereof.

49. A method according to claim 48, wherein:
W is CR$^6$;
R$^1$ is alkyl, haloalkyl, cycloalkyl or naphthyl; or R$^1$ is phenyl which is unsubstituted or is substituted by halogen, alkyl, haloalkyl, alkoxy, haloalkoxy or NO$_2$; R$^1$ is —CH$_2$R$^7$ wherein R$^7$ is phenyl which is unsubstituted or is substituted by halogen, alkyl or alkoxy; or R$^1$ is —CH$_2$CH$_2$R$^7$ wherein R$^7$ is phenyl;
R$^2$ is NR$^{12}$R$^{13}$ or —N=CHR$^{14}$;
R$^3$ and R$^6$ are each independently hydrogen or halogen;
R$^4$ is hydrogen and R$^5$ is halogen, CF$_3$, OCF$_3$ or SF$_5$; or R$^4$ is CF$_3$ and R$^5$ is hydrogen;
R$^{12}$ is hydrogen, alkyl or —C(O)R$^{15}$;
R$^{13}$ is hydrogen or alkyl;
R$^{14}$ is alkoxy;
R$^{15}$ is alkyl; and
n is one or two;
or an agriculturally acceptable salt thereof.

50. A method for the control of pests at a locus, said method comprising applying to said locus a pesticidally effective amount of a pesticidal composition as claimed in claim 23.

51. A method for the control of pests at a locus, said method comprising applying to said locus a pesticidally effective amount of a pesticidal composition as claimed in claim 24.

52. A method for the control of pests at a locus, said method comprising applying to said locus a pesticidally effective amount of a pesticidal composition as claimed in claim 25.

53. A method for the control of pests at a locus, said method comprising applying to said locus a pesticidally effective amount of a pesticidal composition as claimed in claim 26.

54. A method for the control of pests at a locus, said method comprising applying to said locus a pesticidally effective amount of a pesticidal composition as claimed in claim 27.

55. A method according to claim 28, wherein the locus is an area used, or to be used, for the growing of plants and wherein said compound is applied to said locus at an application rate of from about 2 g/ha to about 5 kg/ha.

56. A method according to claim 29, wherein the locus is an area used, or to be used, for the growing of plants and wherein said compound is applied to said locus at an application rate of from about 2 g/ha to about 5 kg/ha.

57. A method according to claim 47, wherein the locus is an area used, or to be used, for the growing of plants and wherein said compound is applied to said locus at an application rate of from about 2 g/ha to about 5 kg/ha.

58. A method according to claim 48, wherein the locus is an area used, or to be used, for the growing of plants and wherein said compound is applied to said locus at an application rate of from about 2 g/ha to about 5 kg/ha.

59. A method according to claim 49, wherein the locus is an area used, or to be used, for the growing of plants and wherein said compound is applied to said locus at an application rate of from about 2 g/ha to about 5 kg/ha.

60. A plant seed, treated or coated with a pesticidally effective amount of a compound as claimed in claim 1.

61. A plant seed, treated or coated with a pesticidally effective amount of a compound as claimed in claim 2.

62. A plant seed, treated or coated with a pesticidally effective amount of a compound as claimed in claim 20.

63. A plant seed, treated or coated with a pesticidally effective amount of a compound as claimed in claim 21.

64. A plant seed, treated or coated with a pesticidally effective amount of a compound as claimed in claim 22.

65. A plant seed, treated or coated with a pesticidally effective amount of a pesticidal composition as claimed in claim 23.

66. A plant seed, treated or coated with a pesticidally effective amount of a pesticidal composition as claimed in claim 24.

67. A plant seed, treated or coated with a pesticidally effective amount of a pesticidal composition as claimed in claim 25.

68. A plant seed, treated or coated with a pesticidally effective amount of a pesticidal composition as claimed in claim 26.

69. A plant seed, treated or coated with a pesticidally effective amount of a pesticidal composition as claimed in claim 27.

70. A veterinary composition comprising a pesticidally effective, veterinarily acceptable amount of a compound as claimed in claim 1 and at least one member selected from the group consisting of a veterinarily acceptable carrier and a veterinarily acceptable surface-active agent.

71. A veterinary composition comprising a pesticidally effective, veterinarily acceptable amount of a compound as claimed in claim 2 and at least one member selected from the group consisting of a veterinarily acceptable carrier and a veterinarily acceptable surface-active agent.

72. A veterinary composition comprising a pesticidally effective, veterinarily acceptable amount of a compound as claimed in claim 20 and at least one member selected from the group consisting of a veterinarily acceptable carrier and a veterinarily acceptable surface-active agent.

73. A veterinary composition comprising a pesticidally effective, veterinarily acceptable amount of a compound as claimed in claim 21 and at least one member selected from the group consisting of a veterinarily acceptable carrier and a veterinarily acceptable surface-active agent.

74. A veterinary composition comprising a pesticidally effective veterinarily acceptable amount of a compound as claimed in claim 22 and at least one member selected from the group consisting of a veterinarily acceptable carrier and a veterinarily acceptable surface-active agent.

75. A process for the preparation of a compound as claimed in claim 1, said process comprising reacting a compound of the formula (II):

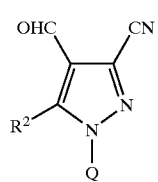

(II)

wherein $R^2$ and Q are defined as in claim 1, with a thiol of the formula (III):

$R^1SH$ (III)

wherein $R^1$ is defined as in claim 1, in the presence of a Lewis acid, to give a hemithioacetal intermediate of the formula (IV):

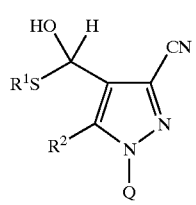

(IV)

which is isolated or unisolated; followed by reducing the resultant isolated or unisolated compound of formula (IV) with a reducing agent, to give the corresponding compound of formula (I) wherein n is zero; or oxidizing a compound of formula (I) wherein n is zero, with a peracid or with hydrogen peroxide, to give the corresponding compound of formula (I) wherein n is one or two.

76. A process for the preparation of a compound as claimed in claim 2, said process comprising reacting a compound of the formula (II):

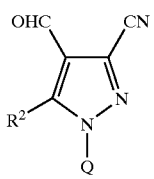

(II)

wherein R² and Q are defined as in claim 2, with a thiol of the formula (III):

R¹SH  (III)

wherein R¹ is defined as in claim 2, in the presence of a Lewis acid, to give a hemithioacetal intermediate of the formula (IV):

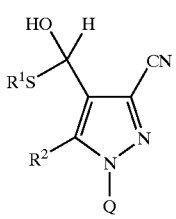

(IV)

which is isolated or unisolated; followed by reducing the resultant isolated or unisolated compound of formula (IV) with a reducing agent, to give the corresponding compound of formula (I) wherein n is zero; or oxidizing a compound of formula (I) wherein n is zero, with a peracid or with hydrogen peroxide, to give the corresponding compound of formula (I) wherein n is one or two.

77. A process for the preparation of a compound as claimed in claim 20, said process comprising reacting a compound of the formula (II):

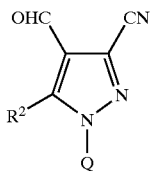

(II)

wherein R² and Q are defined as in claim 20, with a thiol of the formula (III):

R¹SH  (III)

wherein R¹ is defined as in claim 20, in the presence of a Lewis acid, to give a hemithioacetal intermediate of the formula (IV):

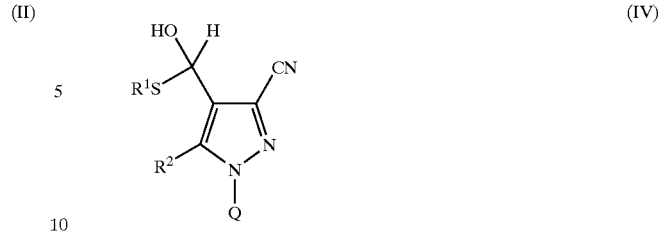

(IV)

which is isolated or unisolated; followed by reducing the resultant isolated or unisolated compound of formula (IV) with a reducing agent, to give the corresponding compound of formula (I) wherein n is zero; or oxidizing a compound of formula (I) wherein n is zero, with a peracid or with hydrogen peroxide, to give the corresponding compound of formula (I) wherein n is one or two.

78. A process for the preparation of a compound as claimed in claim 21, said process comprising reacting a compound of the formula (II):

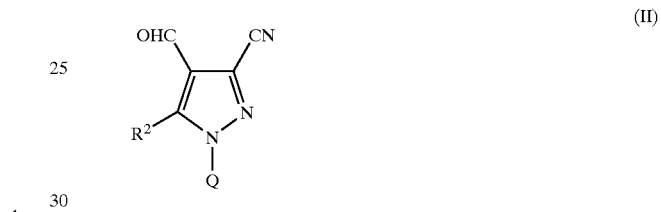

(II)

wherein R² and Q are defined as in claim 21, with a thiol of the formula (III):

R¹SH  (III)

wherein R¹ is defined as in claim 21, in the presence of a Lewis acid, to give a hemithioacetal intermediate of the formula (IV):

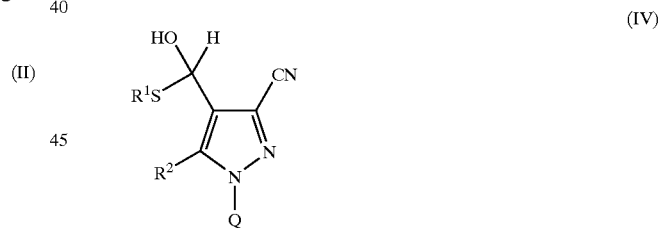

(IV)

which is isolated or unisolated; followed by reducing the resultant isolated or unisolated compound of formula (IV) with a reducing agent, to give the corresponding compound of formula (I) wherein n is zero; or oxidizing a compound of formula (I) wherein n is zero, with a peracid or with hydrogen peroxide, to give the corresponding compound of formula (I) wherein n is one or two.

* * * * *